US011007255B2

(12) United States Patent
Yan

(10) Patent No.: US 11,007,255 B2
(45) Date of Patent: May 18, 2021

(54) CANCER VACCINES AND METHODS OF TREATMENT USING THE SAME

(71) Applicant: Inovio Pharmaceuticals, Inc., Plymouth Meeting, PA (US)

(72) Inventor: Jian Yan, Wallingford, PA (US)

(73) Assignee: Inovio Pharmaceuticals, Inc., Plymouth Meeting, PA (US)

( * ) Notice: Subject to any disclaimer, the term of this patent is extended or adjusted under 35 U.S.C. 154(b) by 237 days.

(21) Appl. No.: 16/075,527

(22) PCT Filed: Feb. 3, 2017

(86) PCT No.: PCT/US2017/016557
§ 371 (c)(1),
(2) Date: Aug. 3, 2018

(87) PCT Pub. No.: WO2017/136758
PCT Pub. Date: Aug. 10, 2017

(65) Prior Publication Data

US 2019/0038729 A1 Feb. 7, 2019

Related U.S. Application Data

(60) Provisional application No. 62/291,601, filed on Feb. 5, 2016.

(51) Int. Cl.

*A61K 39/00* (2006.01)
*A61P 35/00* (2006.01)
*C07K 14/47* (2006.01)
*A61K 38/20* (2006.01)
*A61K 9/00* (2006.01)
*A61K 39/39* (2006.01)

(52) U.S. Cl.

CPC ........ *A61K 39/0011* (2013.01); *A61K 9/0009* (2013.01); *A61K 38/20* (2013.01); *A61K 39/001157* (2018.08); *A61K 39/39* (2013.01); *A61P 35/00* (2018.01); *C07K 14/47* (2013.01); *C12Y 207/07049* (2013.01); *A61K 2039/53* (2013.01); *A61K 2039/54* (2013.01); *A61K 2039/552* (2013.01); *A61K 2039/55527* (2013.01); *A61K 2039/572* (2013.01)

(58) Field of Classification Search

CPC ........ A61K 39/0011; A61K 39/001157; A61K 38/20; A61K 9/0009; A61K 39/39; A61K 2039/552; A61K 2039/572; A61K 2039/53; A61K 2039/54; A61K 2039/55527; A61K 2039/585; C07K 14/47; C12Y 207/07049; A61P 35/00; C12N 9/1276

See application file for complete search history.

(56) References Cited

U.S. PATENT DOCUMENTS

2014/0186384 A1* 7/2014 Weiner .................... C12N 7/00 424/188.1

FOREIGN PATENT DOCUMENTS

WO 2014154905 A1 10/2014
WO 2018217982 A1 11/2018

OTHER PUBLICATIONS

Nasir et al., Gene 336 (2004) 105-113. (Year: 2004).*
Peruzzi et al., Vaccine 28 (2010) 1201-1208. (Year: 2010).*
Regan et al., The Veterinary Journal 207 (2016) 20-28 (Year: 2016).*
Zhao et al., Gene Aug. 15, 2015; 568(1): 8-18 (Year: 2015).*
Peruzzi et al., Molecular Therapy 2010 vol. 18 No. 8, 1559-1567 (Year: 2010).*
Yan et al., Cancer Immunol Res (2013); 1(3); 179-89. (Year: 2013).*
Peruzzi et al., "A Vaccine Targeting Telomerase Enhances Survival of Dogs Affected by B-cell Lymphoma" Molecular Therapy, vol. 18, No. 8, XP002703572, Aug. 2010, pp. 1559-1567.

* cited by examiner

*Primary Examiner* — Brad Duffy
*Assistant Examiner* — Cheom-Gil Cheong
(74) *Attorney, Agent, or Firm* — BakerHostetler

(57) ABSTRACT

The invention provides a vaccine comprising a nucleic acid molecule that encodes a dog telomerase reverse transcriptase (dTERT) antigen, as well as methods of using the vaccine to induce an immune response against a TERT and to treat cancer in a mammal.

16 Claims, 10 Drawing Sheets

Specification includes a Sequence Listing.

A

B

CANCER VACCINES AND METHODS OF TREATMENT USING THE SAME

CROSS REFERENCE TO RELATED APPLICATION(S)

This patent application is the National Stage Application of International Patent Application No. PCT/US2017/016557, filed Feb. 3, 2017, which claims priority to U.S. Provisional Patent Application No. 62/291,601, filed on Feb. 5, 2016. The above referenced applications are hereby incorporated by reference in their entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: one 47,931 bytes ASCII (Text) file named "VGX0151WO_ST25.txt," created on Feb. 3, 2017.

TECHNICAL FIELD

Disclosed herein are compositions and methods for treating cancer and vaccines that treat and provide protection against tumor growth.

BACKGROUND

Cancer is among the leading causes of death worldwide, and in the United States, is the second most common cause of death, accounting for nearly one of every four deaths. Cancer arises from a single cell that has transformed from a normal cell into a tumor cell. Such a transformation is often a multistage process, progressing from a pre-cancerous lesion to malignant tumors. Multiple factors contribute this progression, including aging, genetic contributions, and exposure to external agents such as physical carcinogens (e.g., ultraviolet and ionizing radiation), chemical carcinogens (e.g., asbestos, components of tobacco smoke, etc.), and biological carcinogens (e.g., certain viruses, bacteria, and parasites).

Prevention, diagnosis, and treatment of cancer may take many different forms. Prevention may include screening for pre-disposing factors (e.g., specific genetic variants), altering behavior (e.g., smoking, diet, and amount of physical activity), and vaccination against viruses (e.g., human papilloma virus hepatitis B virus). Treatment may include chemotherapy, radiation therapy, and surgical removal of a tumor or cancerous tissue. Despite the availability of numerous prevention and treatment methods, such methods often meet with limited success in effectively preventing and/or treating the cancer at hand.

Accordingly, a need exists for the identification and development of compositions and methods for the prevention and/or treatment of cancer. Furthermore, more effective treatments are required to delay disease progression and/or decrease mortality in subjects suffering from cancer.

SUMMARY OF INVENTION

Aspects of the invention include vaccines comprising a nucleic acid molecule encoding a telomerase reverse transcriptase cancer antigen. The vaccine comprises a polynucleotide sequence selected from the group consisting of: the polynucleotide sequence of SEQ ID NO: 1, a polynucleotide sequence that is at least 95% identical to SEQ ID NO: 1; a polynucleotide sequence encoding the amino acid sequence of SEQ ID NO: 2; and a polynucleotide sequence encoding an amino acid sequence that is at least 95% identical to SEQ ID NO: 2, or any combination thereof.

Other aspects of the invention include methods of inducing an immune response against telomerase reverse transcriptase (TERT) in a mammal, which method comprises administering the vaccine of claim 1 to a mammal in need thereof, whereby the nucleic acid molecule is expressed in the mammal and one or more of the following immune responses are induced in the mammal: (a) a humoral immune response specific to TERT, (b) an inflammatory response comprising increased levels of tumor necrosis factor-α (TNF-α) and interferon-γ (IFN-γ) as compared to an untreated mammal, and (c) a cellular immune response specific to TERT.

Some aspects of the invention further include methods of treating a cancer in a mammal, which method comprises administering to a mammal in need thereof a composition comprising the above-described vaccine and a pharmaceutically-acceptable carrier, whereby the polynucleotide is expressed in the mammal and the cancer is treated.

BRIEF DESCRIPTION OF THE DRAWINGS

Sequences disclosed herein, and as further described in the drawings, are as follows:

SEQ ID NO:1 corresponds to synthetic consensus (SYNCON) dTERT.

SEQ ID NO:2 corresponds to the amino acids sequence encoded by SEQ ID NO:1.

SEQ ID NO:3 corresponds to the nucleic acid sequence for plasmid pGX1414 (pGX0001 containing SEQ ID NO:1 as an insert).

SEQ ID NO:4 corresponds to the nucleic acid sequence encoding dTERT-PL (SEQ ID NO:5), which is dog telomerase reverse transcriptase (dTERT) polypeptide having seven point mutations that abolish telomerase activity (substitutions: R579Y, D996Y, K633A, R638A, D719A, Y724A and D876A. SEQ ID NO:4 is the pGX1415 insert.

SEQ ID NO:5 (dTERT-PL) corresponds to the amino acid sequence encoded by SEQ ID NO:4.

SEQ ID NO:6 corresponds to an immunodominant epitope of SEQ ID NO:5.

SEQ ID NO:7 corresponds to the amino acid sequence for dTERT.

Figure 1:
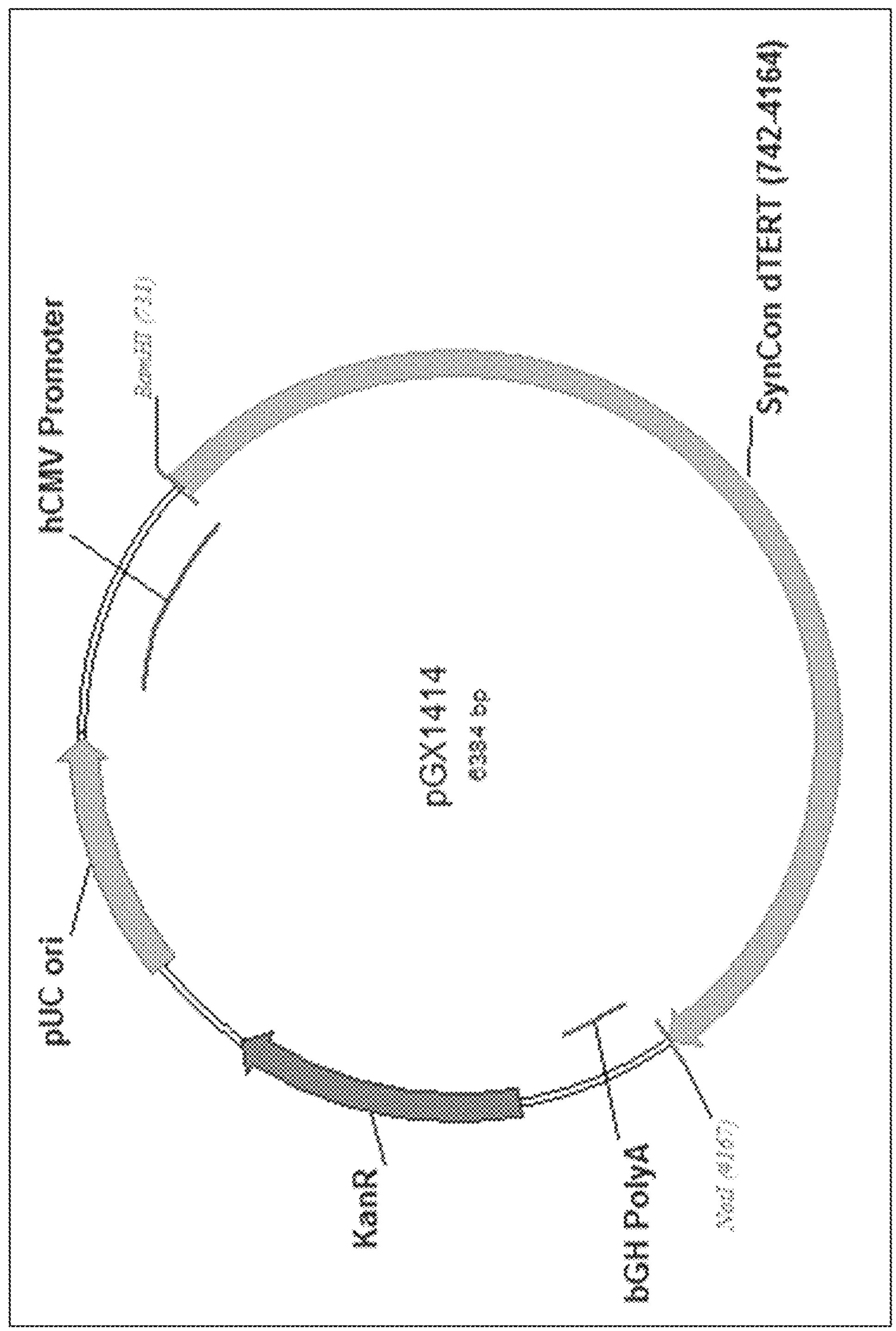

FIG. 1 is a diagram of the plasmid vector pGX1414 (SEQ ID NO:3) described in Example 1.

Figure 2:
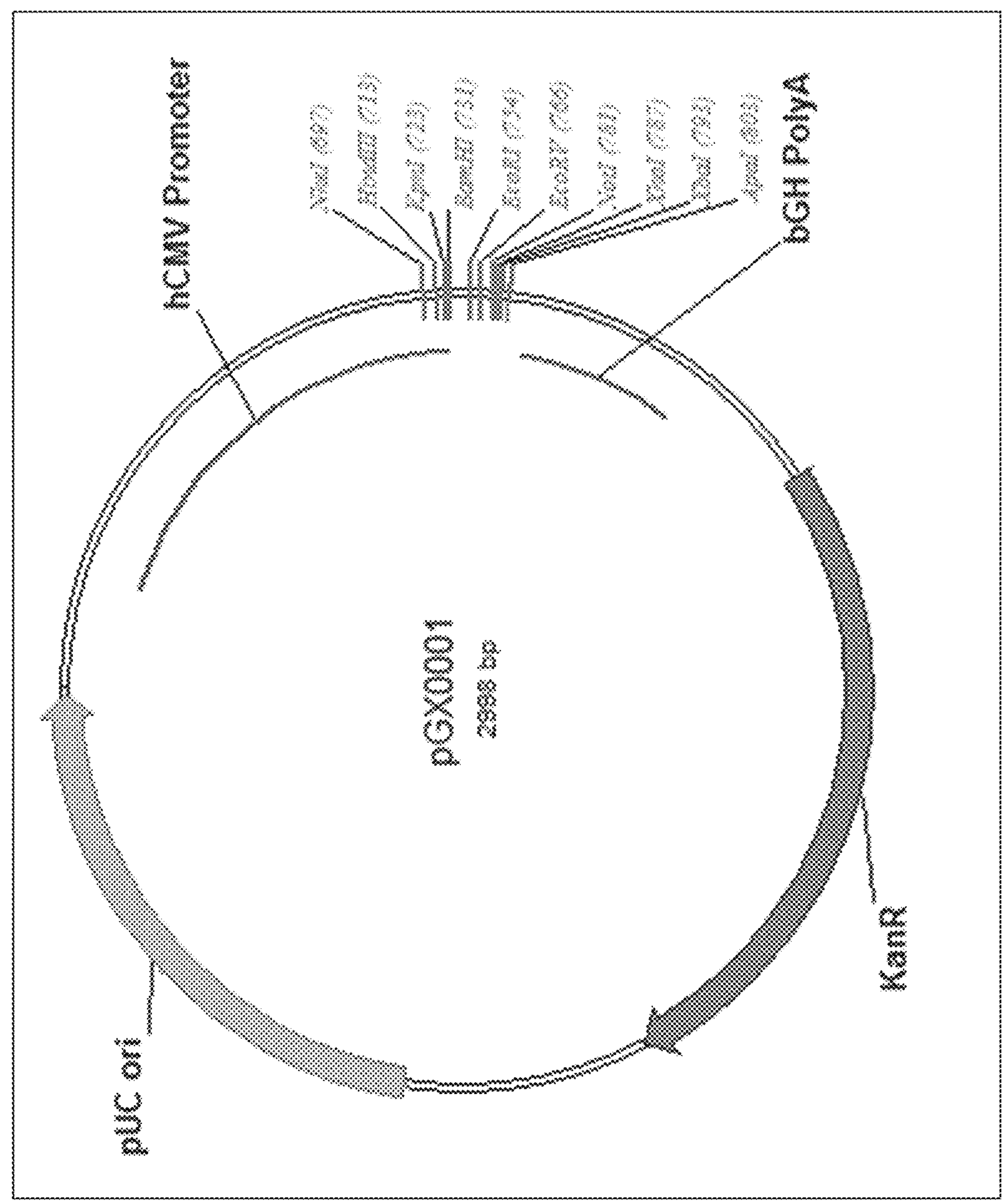

FIG. 2 is a diagram of the plasmid vector pGX0001 described in Example 1.

Figure 3:
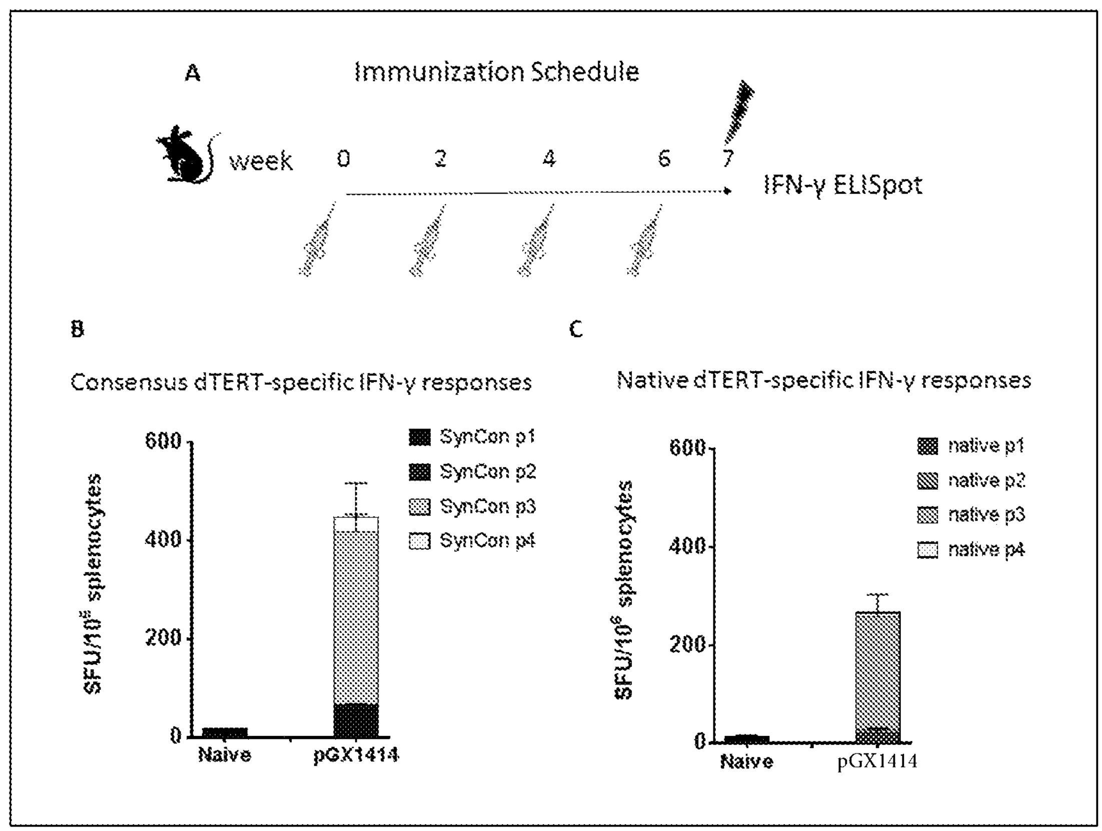

FIG. 3A is a diagram of the pGX1414 (SEQ ID NO:3) immunization schedule in mice as described in Example 2. FIG. 3B is a graph illustrating the total SYNCON dTERT (SEQ ID NO:1)-specific IFN-γ responses induced by pGX1414 (SEQ ID NO:3). FIG. 3C is a graph illustrating the total native dTERT-specific IFN-γ responses induced by pGX1414. Frequencies of IFN-γ-secreting cells/$10^6$ splenocytes after four immunizations with pGX1414 were determined by IFN-γ ELISpot assay. Splenocytes from each mouse (five mice per group) were stimulated with either SYNCON dTERT peptide (SEQ ID NO:2) or native dTERT peptide (SEQ ID NO:7). Results are presented as mean±SEM.

Figure 4:
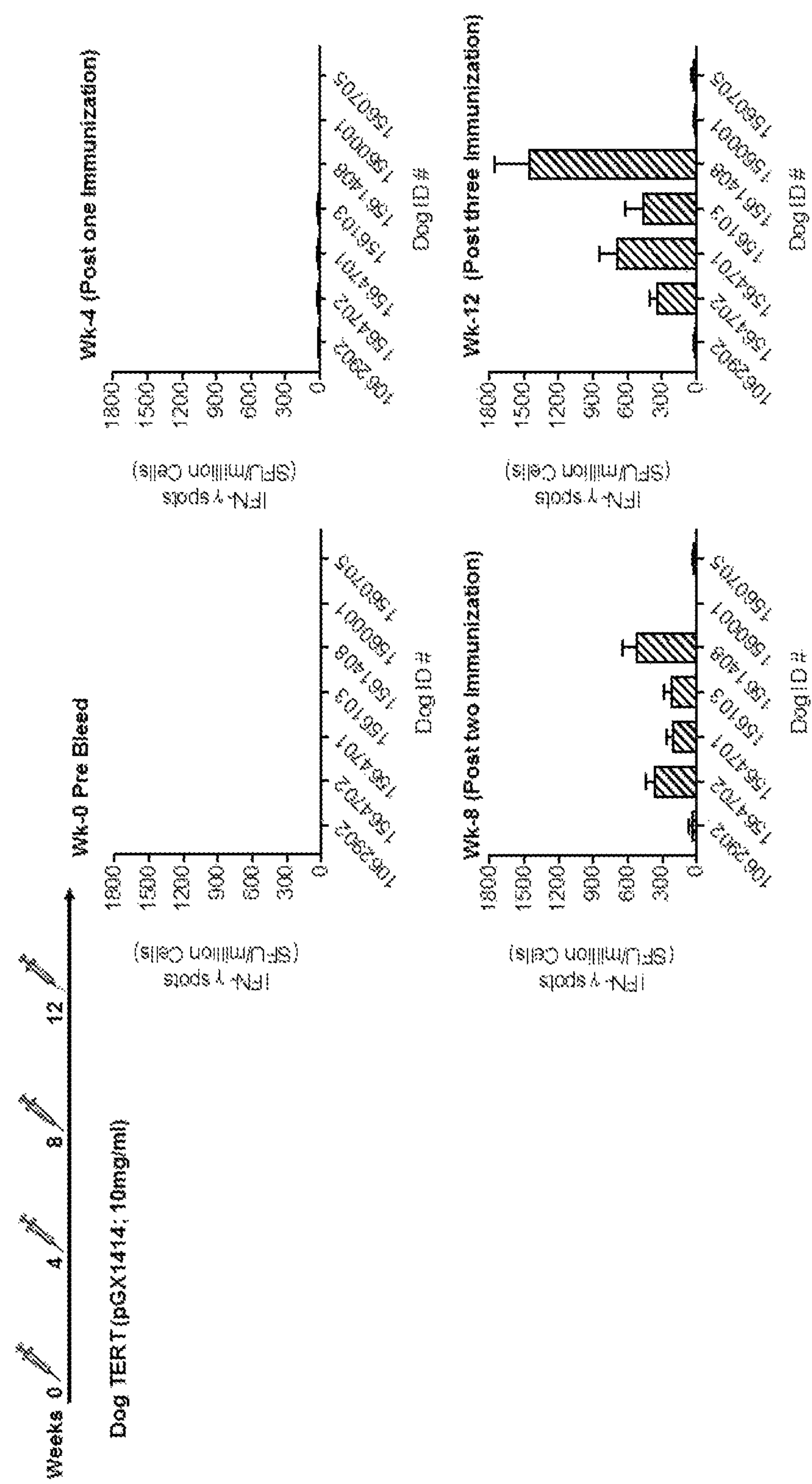

FIG. 4 shows enzyme-linked immunospot (ELISpot) results from dog TERT vaccination program. Seven dogs were immunized with pGX1414, at 10 mg/ml. Results are shown at week 0 (no immunization, pre-bleed), week 4 (post pre-bleed immunization #1), week 8 (post pre-bleed immunization #2), and week 12 (post pre-bleed immunization #3). The results show that TERT DNA vaccination induces cell mediated immune responses in dog.

FIG. 5A is a diagram of the plasmid vector pGX1415, which is plasmid vector pGX0001 containing SEQ ID NO:4 as an insert. FIG. 5B shows gel electrophoresis results of plasmid pGX1415 digested with the named enzymes.

Figure 6:
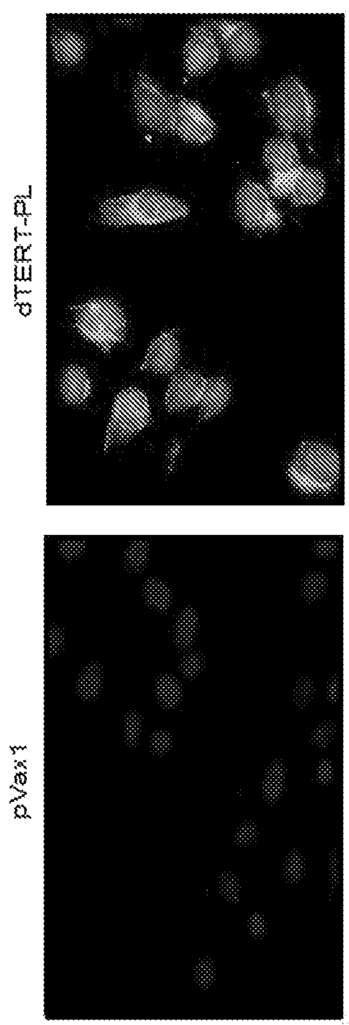

FIG. 6 shows high level of expression of Dog TERT-PL (SEQ ID NO:4, which encodes SEQ ID NO:5) in transfected cells. 293T cells were transfected with pVax1 or Dog TERT-PL DNA construct (10 μg) encoding SEQ ID NO:5. 2 days post transfection, cells were fixed and stained with anti-TERT antibody for expression of TERT in transfected cells.

Figure 7:
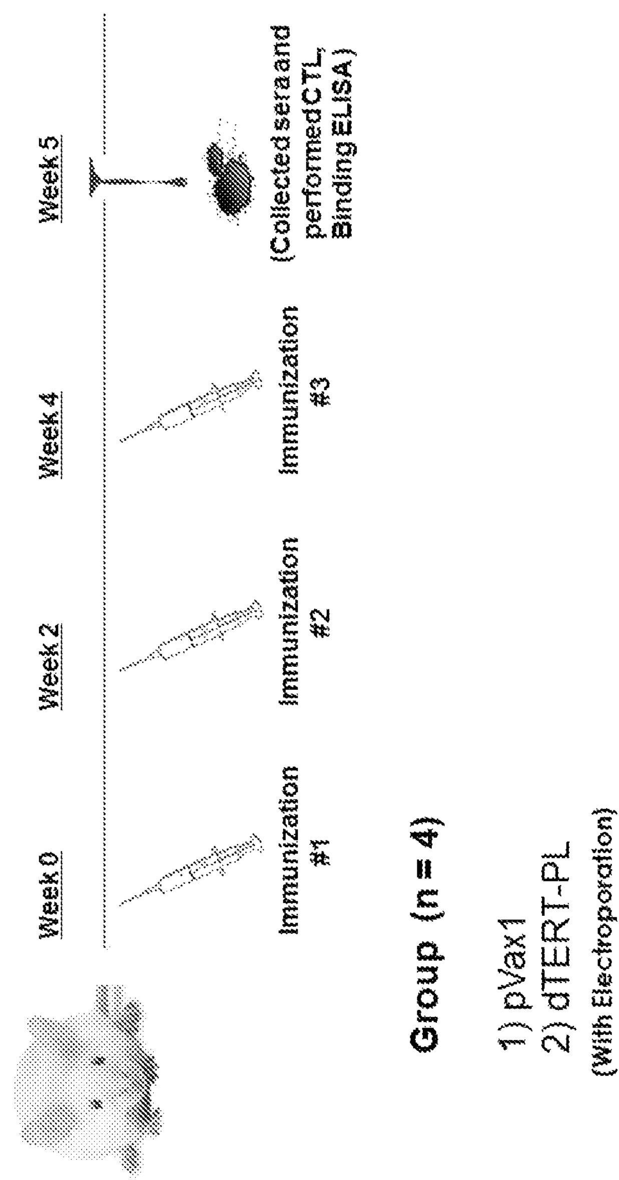

FIG. 7 is a diagram of the immunization schedule for dTERT-PL (administered as pGX1415).

Figure 8:
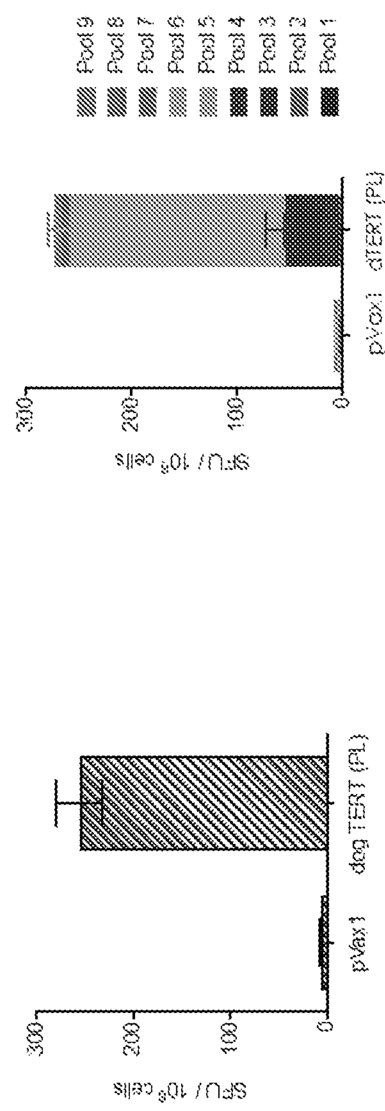

FIG. 8 shows induction of cellular immune responses by dTERT-PL (administered as pGX1415) vaccine in mice. Cellular immune responses induced by dTERT-PL (pGX1415) were examined in C57BL/6 mice. Total dTERT-specific IFN-γ responses one week after third immunization from vaccine (25 μg). Splenocytes from each mouse (4 mice per group) were stimulated with dTERT peptide pools separately. Data suggesting the long-term persistence of immune response after dTERT-PL DNA vaccination. Results are presented combined peptide pools as mean±SEM.

Figure 9:
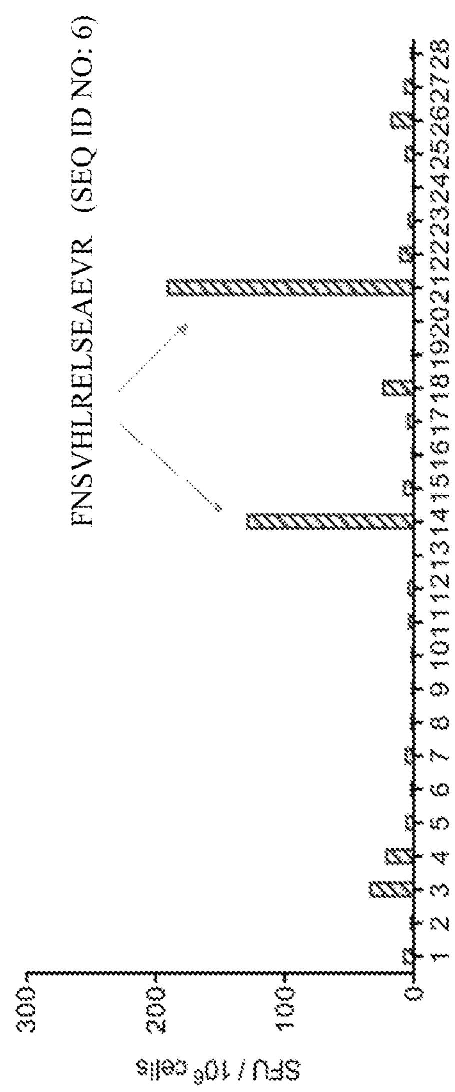

FIG. 9 shows a prediction of a dominant cytotoxic T lymphocyte (CTL) epitope of dTERT-PL (pGX1415) DNA vaccine in C57/BL6 mice. Dog specific dTERT-PL DNA plasmid elicits significant cellular immune responses in mice after three vaccinations with electroporation. High levels of IFN-γ T cell specific immunodominant and subdominant epitopes of dog TERT were observed in the spleen. Epitope FNSVHLRELSEAEVR (SEQ ID NO:6) was identified (via epitope mapping using ELIspot) as an immunodominant epitope of the dTERT-PL DNA vaccine. The number of matrix pools are identified on the X-axis.

Figure 10:
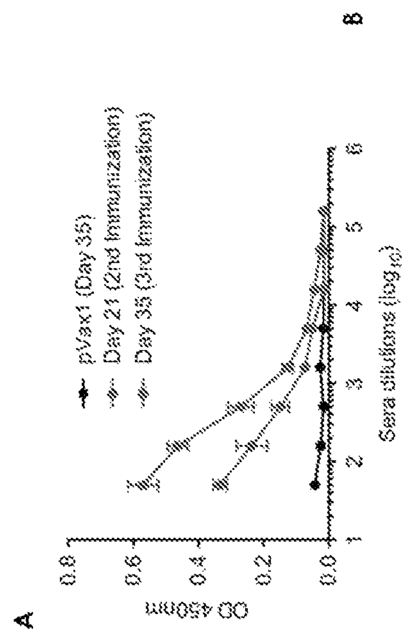
Figure 10:
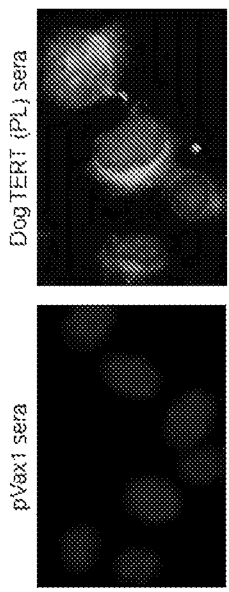

FIG. 10 shows humoral immune response after immunization with DNA construct (pGX1415) expressing dog TERT (SEQ ID NO:5). (A) Total IgG antibody tiers in the sera of the immunized mice as shown by enzyme-linked immunosorbent assay (ELISA). Each group of mice (n=5) was immunized with 50 μg of dTERT-PL DNA. (B) Specificity was detected by immunofluorescence assay (IFA) in 293T cells transfected with DNA plasmid vaccine encoding the dTERT, treated with immune serum from the mice. Anti-TERT total IgG levels by ELISA and specificity by IFA were observed in dTERT-PL vaccinated mice sera compared with pVax1 sera.

DETAILED DESCRIPTION

An aspect of the invention includes a vaccine that can be customized to treat or prevent particular cancers and tumors. Antigens have been designed for the cancer related antigen telomerase reverse transcriptase isolated from *Canis familiaris* (dog), referred to herein as dogTERT, dog-TERT, or dTERT. For example, antigen consensus (e.g. SEQ ID NO:4, which encodes SEQ ID NO:5) sequences have been designed for the cancer related antigen dTERT. Canine cancers occur with an incidence similar to that of humans and share many features with human cancers, including, for example, histological appearance, tumor genetics, biological behavior, and response to conventional therapies. As observed in humans, TERT activity is largely confined to tumor tissues and absent in the majority of normal dog tissues. As such, the invention utilizes dTERT consensus sequences as antigens for cancer immunotherapy in mammals, especially canines. The dTERT antigen can be used in combination with other cancer related antigens, such as, for example, tyrosinase (Tyr), preferentially expressed antigen in melanoma (PRAME), tyrosinase related protein 1 (Tyrp1), cancer testes antigen (NY-ESO-1), hepatitis B virus antigen, and Wilms tumor 1 antigen (WT-1) in the inventive vaccine to allow for customized vaccine prevention and treatment of particular cancers. The vaccine can provide any combination of particular cancer antigens for the particular prevention or treatment of the cancer of a subject that is in need of treatment.

The recombinant cancer antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up-regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and immune checkpoint molecules.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting. The terminology used herein is for the purpose of describing particular embodiments only and is not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

"Adjuvant" as used herein means any molecule added to the DNA plasmid vaccines described herein to enhance the immunogenicity of the antigens encoded by the DNA plasmids and the encoding nucleic acid sequences described hereinafter.

"Antibody" as used herein means an antibody of classes IgG, IgM, IgA, IgD or IgE, or fragments, or derivatives thereof, including Fab, F(ab')2, Fd, and single chain antibodies, diabodies, bispecific antibodies, bifunctional antibodies and derivatives thereof. The antibody can be an antibody isolated from the serum sample of mammal, a polyclonal antibody, affinity purified antibody, or mixtures thereof which exhibits sufficient binding specificity to a desired epitope or a sequence derived therefrom.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered.

"Complement" or "complementary" as used herein means a nucleic acid can mean Watson-Crick (e.g., A-T/U and C-G) or Hoogsteen base pairing between nucleotides or nucleotide analogs of nucleic acid molecules.

"Consensus" or "consensus sequence" as used herein means a polypeptide sequence that is based on analysis of an alignment of multiple sequences for the same gene from different organisms. Nucleic acid sequences that encode a consensus polypeptide sequence can be prepared. Vaccines comprising proteins that comprise consensus sequences and/or nucleic acid molecules that encode such proteins can be used to induce broad immunity against an antigen.

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Fragment" as used herein with respect to nucleic acid sequences means a nucleic acid sequence or a portion thereof, that encodes a polypeptide capable of eliciting an immune response in a mammal that cross reacts with an antigen disclosed herein. The fragments can be DNA fragments selected from at least one of the various nucleotide sequences that encode protein fragments set forth below. Fragments can comprise at least 10%, at least 20%, at least 30%, at least 40%, at least 50%, at least 60%, at least 70%, at least 80%, at least 90%, or at least 95% of one or more of the nucleic acid sequences set forth below.

"Fragment" or "immunogenic fragment" with respect to polypeptide sequences means a polypeptide capable of eliciting an immune response in a mammal that cross reacts with an antigen disclosed herein. The fragments can be polypeptide fragments selected from at least one of the various amino acids sequences below. Fragments of consensus proteins can comprise at least 10%, at least 20%, at least 30%, at least 40%, at least 50%, at least 60%, at least 70%, at least 80%, at least 90% or at least 95% of a consensus protein.

As used herein, the term "genetic construct" refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

The term "homology," as used herein, refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous." When used in reference to a double-stranded nucleic acid sequence such as a cDNA or genomic clone, the term "substantially homologous," as used herein, refers to a probe that can hybridize to a strand of the double-stranded nucleic acid sequence under conditions of low stringency. When used in reference to a single-stranded nucleic acid sequence, the term "substantially homologous," as used herein, refers to a probe that can hybridize to (i.e., is the complement of) the single-stranded nucleic acid template sequence under conditions of low stringency.

The term "immune checkpoint inhibitor," as used herein, refers to any nucleic acid or protein that prevents the suppression of any component in the immune system, such as MHC class presentation, T cell presentation and/or differentiation, B cell presentation and/or differentiation, and cytokine, chemokine or signaling for immune cell proliferation and/or differentiation.

"Identical" or "identity" as used herein in the context of two or more nucleic acids or polypeptide sequences means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Immune response" as used herein means the activation of a host's immune system, e.g., that of a mammal, in response to the introduction of antigen. The immune response can be in the form of a cellular or humoral response, or both.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the amino terminus (i.e., N terminus) of the protein.

"Stringent hybridization conditions" as used herein means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5-10° C. lower than the thermal melting point (Tm) for the specific sequence at a defined ionic strength pH. The Tm can be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" as used herein can mean a mammal that wants to or is in need of being immunized with the herein described vaccines. The mammal can be a dog, human, chimpanzee, cat, horse, cow, mouse, or rat.

"Substantially complementary" as used herein means that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

"Substantially identical" as used herein means that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

"Treatment" or "treating" as used herein can mean protecting an animal from a disease through means of preventing, suppressing, repressing, or completely eliminating the disease. Preventing the disease involves administering a vaccine of the present invention to an animal prior to onset of the disease. Suppressing the disease involves administering a vaccine of the present invention to an animal after induction of the disease but before its clinical appearance. Repressing the disease involves administering a vaccine of the present invention to an animal after clinical appearance of the disease.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art (see, e.g., Kyte et al., J. *Mol. Biol.,* 157: 105-132 (1982)). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity (see, e.g., U.S. Pat. No. 4,554, 101). Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome (BAC), or yeast artificial chromosome (YAC). A vector can be a DNA or RNA vector. A vector can be a self-replicating extrachromosomal vector, and preferably, is a DNA plasmid. The vector can contain or include one or more heterologous nucleic acid sequences.

2. Vaccine

The present invention is directed to an anti-cancer vaccine. The vaccine can comprise one or more cancer antigens or one or more nucleic acid molecules encoding one or more cancer antigens as described herein. The vaccine can prevent tumor growth. The vaccine can reduce tumor growth. The vaccine can prevent metastasis of tumor cells. In some instances, the vaccine can be targeted to treat liver cancer, prostate cancer, melanomas, blood cancers (e.g., lymphoma, multiple myeloma, and leukemia), head and neck cancer, glioblastoma, recurrent respiratory papillomatosis (RRP), anal cancer, cervical cancer, brain cancer, renal cell carcinoma, lung cancers (e.g., non-small cell lung carcinoma), bladder cancer, breast cancer, uterine cancer, testicular cancer, colon cancer, gall bladder cancer, laryngeal cancer, thyroid cancer, stomach cancer, salivary gland cancer, or pancreatic cancer.

The first step in development of the vaccine is to identify a cancer antigen that is not recognized by the immune system and is a self-antigen. The identified cancer antigen is changed from a self-antigen to a foreign antigen in order to be recognized by the immune system. The redesign of the nucleic acid and amino acid sequence of the recombinant cancer antigen from a self to a foreign antigen breaks tolerance of antigen by the immune system. In order to break tolerance, several redesign measures can be applied to the cancer antigen as described below.

One method for designing a recombinant nucleic acid sequence encoding a consensus cancer antigen is introducing mutations that change particular amino acids in the overall amino acid sequence of the native cancer antigen. The introduction of mutations does not alter the cancer antigen so much that it cannot be universally applied across animal subjects, but changes it enough that the resulting amino acid sequence breaks tolerance or is considered a foreign antigen in order to generate an immune response. Another method may be creating a consensus recombinant cancer antigen that has 95%, 96%, 97%, 98%, 99% or greater nucleic acid or amino acid sequence identity to the corresponding native cancer antigen. The native cancer antigen is the antigen normally associated with the particular cancer or cancer tumor. Depending upon the cancer antigen, the consensus sequence of the cancer antigen can be across mammalian species or within subtypes of a species or across viral strains or serotypes. Some cancer antigens do not vary greatly from the wild type amino acid sequence of the cancer antigen. Some cancer antigens have nucleic acid/amino acid sequences that are so divergent across species, that a consensus sequence cannot be generated. In these instances, a recombinant cancer antigen that will break tolerance and generate an immune response is generated that has 95%, 96%, 97%, 98%, 99% or greater nucleic acid or amino acid sequence identity to the corresponding native cancer antigen.

The recombinant cancer antigen of the vaccine is not recognized as self, therefore breaking tolerance. The breaking of tolerance can induce antigen-specific T cell and/or high titer antibody responses, thereby inducing or eliciting an immune response that is directed to, or reactive against, the cancer or tumor expressing the antigen. In some embodiments, the induced or elicited immune response can be a cellular response, humoral response, or both cellular and humoral immune responses. In some embodiments, the induced or elicited cellular immune response can include induction or secretion of interferon-gamma (IFN-γ) and/or tumor necrosis factor alpha (TNF-α). In this regard, the inventive vaccine can induce an immune response in a mammal comprising increased levels of tumor necrosis factor-α (TNF-α) and interferon-γ (IFN-γ) as compared to an untreated mammal that has not received the vaccine. In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and immune checkpoint molecules.

In a particular embodiment, the vaccine can mediate clearance or prevent growth of tumor cells by inducing (1) humoral immunity via B cell responses to generate antibodies that block monocyte chemoattractant protein-1 (MCP-1) production, thereby retarding myeloid derived suppressor cells (MDSCs) and suppressing tumor growth; (2) increase cytotoxic T lymphocyte such as $CD8^{+}$ (CTL) to attack and kill tumor cells; (3) increase T helper cell responses; (4) and increase inflammatory responses via IFN-γ and TFN-α, or preferably all of the aforementioned. The vaccine can increase tumor-free survival by 30%, 31%, 32%, 33%, 34%, 35%, 36%, 37%, 38%, 39%, 40%, 41%, 42%, 43%, 44%, and 45%. The vaccine can reduce tumor mass by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% after immunization. The vaccine can prevent and block increases in monocyte chemoattractant protein 1 (MCP-1), a cytokine secreted by myeloid derived suppressor cells. The vaccine can increase tumor survival by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60%.

The vaccine can increase a cellular immune response in a subject administered the vaccine by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to a cellular immune response in a subject not administered the vaccine. In some embodiments the vaccine can increase the cellular immune response in the subject administered the vaccine by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to the cellular immune response in the subject not administered the vaccine.

The vaccine can increase interferon gamma (IFN-γ) levels in a subject administered the vaccine by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to IFN-γ levels in a subject not administered the vaccine. In some embodiments the vaccine can increase IFN-γ levels in the subject administered the vaccine by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to IFN-γ levels in the subject not administered the vaccine.

The vaccine can be a DNA vaccine. DNA vaccines are disclosed in, for example, U.S. Pat. Nos. 5,593,972, 5,739,118, 5,817,637, 5,830,876, 5,962,428, 5,981,505, 5,580,859, 5,703,055, and 5,676,594. The DNA vaccine can further comprise elements or reagents that inhibit integration into the chromosome.

The vaccine can be an RNA molecule of the one or more cancer antigens. The RNA vaccine can be introduced into a cell.

The vaccine of the present invention can have features required of effective vaccines such as being safe so that the vaccine itself does not cause illness or death; being protective against illness; inducing neutralizing antibody; inducing protective T cell responses; and providing ease of administration, few side effects, biological stability, and low cost per dose. The vaccine can accomplish some or all of these features by containing the cancer antigen as discussed herein.

a. dTERT

The vaccine of the present invention can comprise the cancer antigen dTERT, a fragment thereof, or a variant thereof dTERT is a dog (*Canis familiaris*) telomerase reverse transcriptase that synthesizes a TTAGGG tag on the end of telomeres to prevent cell death due to chromosomal shortening. The dTERT protein consists of 1123 amino acid residues and contains all the signature motifs of the TERT family members. Sequence comparisons with previously identified mammalian TERT proteins demonstrate that dTERT shows the highest level of sequence similarity to the human TERT (hTERT) protein (see, e.g., Nasir et al., *Gene,* 336(1): 105-13 (2004)). dTERT amino acid sequences have been identified, several of which have been deposited in the GenBank database (see, e.g., GenBank Accession Nos. NP_001026800, NP_001026800.1, XP_004411686, XP_004768446, XP_004812556, EFB14781, XP_004812554, XP_004768447, XP_004440093, XP_004411687, XP_004812555, XP_004274558, NP_937983, AAC51724, NP_001177896, XP_004380340, NP_001039707, XP_003950543, NP_001231229, and DAA17756). Hyperproliferative canine cells and human cells can have abnormally high expression of dTERT and hTERT, respectively. The hTERT cancer antigen is further described in, for example, U.S. Patent Application Publication 2014/0186384 and International Patent Application Publication WO 2014/144885.

Additionally, because hTERT expression in dendritic cells transfected with hTERT genes can induce $CD8^{+}$ cytotoxic T cells and elicit $CD4^{+}$ T cells in an antigen-specific fashion, this suggests that the dTERT antigen can be expressed within antigen presenting cells (APCs) to delay senescence and sustain their capacity to present the antigen of choice in immunotherapeutic methods, such as in those described herein.

The dTERT antigen can be associated with or expressed by any number of canine cancers including, but not limited to, melanoma, prostate cancer, liver cancer, cervical cancer, recurrent respiratory papillomatosis (RRP), anal cancer, head and neck cancer, blood cancers (e.g., leukemia, lymphoma, myeloma), lung carcinomas (e.g., non-small cell lung carcinoma), esophageal squamous cell carcinomas, bladder cancer, colorectal cancer, gastric cancer, hepatocarcinoma, brain cancer (e.g., glioblastoma), pancreatic cancer, synovial carcinoma, testicular cancer, and stomach cancer. Accordingly, the inventive vaccine, when including the dTERT antigen described herein, can be used for treating mammalian subjects (e.g., a canine) suffering from any of the aforementioned cancers.

The dTERT antigen can induce antigen-specific T cell and/or high titer antibody responses, thereby inducing or eliciting an immune response that is directed to, or reactive against the cancer or tumor expressing the antigen. In some embodiments, the induced or elicited immune response can be a cellular response, humoral response, or both cellular and humoral immune responses. In some embodiments, the induced or elicited cellular immune response can include induction or secretion of interferon-gamma (IFN-γ) and/or tumor necrosis factor alpha (TNF-α). In this regard, the inventive vaccine can induce an inflammatory response in a mammal comprising increased levels of tumor necrosis factor-α (TNF-α) and interferon-γ (IFN-γ) as compared to an untreated mammal that has not received the vaccine. In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule.

The dTERT antigen can comprise epitopes that make them particularly effective as immunogens against which anti-dTERT immune responses can be induced. For example, the epitope may comprise the amino acid sequence FNSVHLRELSEAEVR (SEQ ID NO:6). The epitope may be SEQ ID NO:6. The dTERT antigen can comprise the full-length dTERT translation product, a variant thereof, a fragment thereof, or a combination thereof. In one embodiment, the dTERT antigen comprises a consensus amino acid sequence.

The nucleic acid sequence encoding the dTERT antigen or consensus dTERT antigen can be optimized with regards to codon usage and corresponding RNA transcripts. The nucleic acid encoding the dTERT antigen or consensus dTERT antigen can be codon- and/or RNA-optimized for expression in host, preferably mammalian, cells. In some embodiments, the nucleic acid sequence encoding the dTERT antigen or consensus dTERT antigen can include a Kozak sequence (e.g., GCC ACC) to increase the efficiency of translation. The nucleic acid encoding the dTERT antigen or consensus dTERT antigen can include multiple stop codons (e.g., TGA TGA) to increase the efficiency of translation termination.

The nucleic acid encoding the dTERT antigen or consensus dTERT antigen can also encode an immunoglobulin E (IgE) leader sequence. The nucleic acid encoding the dTERT antigen or consensus dTERT antigen can further encode the IgE leader sequence such that the amino acid sequence of the IgE leader sequence is linked to the amino acid sequence of the dTERT antigen or consensus dTERT antigen by a peptide bond. In some embodiments, the nucleic acid encoding the dTERT antigen or consensus dTERT antigen is free of or does not contain a nucleotide sequence encoding the IgE leader sequence.

In some embodiments, the nucleic acid encoding the dTERT antigen or consensus dTERT antigen can be a heterologous nucleic acid sequence and/or contain one or more heterologous nucleic acid sequences. The nucleic acid encoding the dTERT antigen or consensus dTERT antigen can be mutated relative to the wild-type dTERT antigen such that one or more amino acids or residues in the amino acid sequence of the dTERT antigen or consensus dTERT antigen, respectively, is replaced or substituted with another amino acid or residue. The nucleic acid encoding the dTERT antigen or consensus dTERT antigen can be mutated relative to the wild-type dTERT antigen such that one or more residues in the amino acid sequence of the dTERT antigen or consensus dTERT antigen, respectively, are replaced or substituted with another residue, thereby causing the immune system to no longer be tolerant of dTERT in the mammal administered the nucleic acid encoding the dTERT antigen or consensus dTERT antigen, the dTERT antigen or consensus dTERT antigen, or combinations thereof. In one embodiment, for example, the nucleic acid encoding the dTERT antigen or consensus dTERT antigen can be mutated relative to a wild-type dTERT antigen such that the dTERT amino acid sequence comprises one or more of the following amino acid substitutions: R579Y, D996Y, K633A, R638A, D719A, Y724A and/or D876A. Preferably, the nucleic acid encoding dTERT antigen or consensus dTERT antigen is mutated relative to a wild-type dTERT antigen such that the dTERT amino acid sequence comprises all of the following amino acid substitutions: R579Y, D996Y, K633A, R638A, D719A, Y724A and D876A. Not to be bound by any particular theory, it is believed that the substitutions R579Y and D996Y are involved in breaking tolerance (see, e.g., Gross et al., *J. Clin. Invest.,* 113: 425-433 (2004)), and the substitutions K633A, R638A, D719A, Y724A and D876A are involved in abolishing telomerase activity (see, e.g., Weinrich et al., *Nature Genetics,* 17: 498-502 (1997)).

A nucleic acid sequence encoding a consensus dTERT antigen can comprise, for example, SEQ ID NO: 1, which encodes the amino acid sequence of SEQ ID NO: 2. SEQ ID NO:1 encodes the dTERT protein linked to an IgE leader sequence. In other embodiments, the dTERT protein can be free of or not linked to an IgE leader sequence. SEQ ID NO: 1 is set forth in FIG. 1, and SEQ ID NO: 2 is set forth in FIG. 2.

In some embodiments, the nucleic acid sequence encoding the dTERT antigen can comprise at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO: 1. In other embodiments, the nucleic acid sequence encoding the dTERT antigen can be a nucleic acid sequence that encodes an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO: 2. The amino acid sequence of the dTERT antigen can be an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO: 2.

Some embodiments relate to nucleic acid sequences encoding proteins homologous to the dTERT protein, immunogenic fragments of the dTERT protein, and immunogenic fragments of homologous proteins. In other embodiments, the invention provides nucleic acid molecules that encode immunogenic proteins that have up to 95% homology to a sequence, up to 96% homology to a sequence, up to 97% homology to a sequence, up to 98% homology to a sequence, and up to 99% homology to a sequence. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full-length dTERT protein, immunogenic fragments of the dTERT protein, and immunogenic fragments of proteins having identity to the dTERT protein. In other embodiments, the invention provides nucleic acid molecules that encode immunogenic proteins that have up to 80% identity to a full-length dTERT sequence, up to 85% identity to a full-length sequence, up to 90% identity to a full-length dTERT sequence, up to 91% identity to a full-length dTERT sequence, up to 92% identity to a full-length dTERT sequence, up to 93% identity to a full-length dTERT sequence, up to 94% identity to a full-length dTERT sequence, up to 95% identity to a full-length dTERT sequence, up to 96% identity to a full-length dTERT sequence, up to 97% identity to a full-length dTERT sequence, up to 98% identity to a full-length dTERT sequence, and up to 99% identity to a full-length dTERT sequence. Likewise, nucleic acid sequences encoding the immunogenic fragments set forth herein and the immunogenic fragments of proteins with similar percent identities as indicated above to the dTERT proteins set forth herein are also provided.

Some embodiments relate to fragments of SEQ ID NO: 1. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO: 1. Fragments can be at least 95%, at least 96%, at least 97%, at least 98%, or at least 99% homologous to fragments of SEQ ID NO: 1. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO: 1. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

In another embodiment, the amino acid sequence of the dTERT antigen comprises SEQ ID NO: 2, which comprises the amino acid sequence of the dTERT protein linked to an IgE leader. The amino acid sequence of the dTERT protein linked to the IgE leader also may be linked to a human influenza hemagglutinin (HA) tag.

Some embodiments of the invention relate to proteins that are homologous to SEQ ID NO: 2. Some embodiments relate to immunogenic proteins that have 95% homology to the amino acid sequence as set forth in SEQ ID NO: 2. Some embodiments relate to immunogenic proteins that have 96% homology to the amino acid sequence as set forth in SEQ ID NO: 2. Some embodiments relate to immunogenic proteins that have 97% homology to the amino acid sequence as set forth in SEQ ID NO: 2. Some embodiments relate to immunogenic proteins that have 98% homology to the amino acid sequence as set forth in SEQ ID NO: 2. Some embodiments relate to immunogenic proteins that have 99% homology to the amino acid sequence as set forth in SEQ ID NO: 2.

Some embodiments relate to proteins that are identical to SEQ ID NO: 2. Some embodiments relate to immunogenic proteins that have an amino acid sequence that is 80% identical to the full-length amino acid sequence as set forth in SEQ ID NO: 2. Some embodiments relate to immunogenic proteins that have an amino acid sequence that is 85% identical to the full-length amino acid sequence as set forth in SEQ ID NO: 2. Some embodiments relate to immunogenic proteins that have an amino acid sequence that is 90% identical to the full-length amino acid sequence as set forth in SEQ ID NO: 2. Some embodiments relate to immunogenic proteins that have an amino acid sequence that is 91% identical to the full-length amino acid sequence as set forth in SEQ ID NO: 2. Some embodiments relate to immunogenic proteins that have an amino acid sequence that is 92% identical to the full-length amino acid sequence as set forth in SEQ ID NO: 2. Some embodiments relate to immunogenic proteins that have an amino acid sequence that is 93% identical to the full-length amino acid sequence as set forth in SEQ ID NO: 2. Some embodiments relate to immunogenic proteins that have an amino acid sequence that is 94% identical to the full-length amino acid sequence as set forth in SEQ ID NO: 2. Some embodiments relate to immunogenic proteins that have an amino acid sequence that is 95% identical to the full-length amino acid sequence as set forth in SEQ ID NO: 2. Some embodiments relate to immunogenic proteins that have an amino acid sequence that is 96% identical to the full-length amino acid sequence as set forth in SEQ ID NO: 2. Some embodiments relate to immunogenic proteins that have an amino acid sequence that is 97% identical to the full-length amino acid sequence as set forth in SEQ ID NO: 2. Some embodiments relate to immunogenic proteins that have an amino acid sequence that is 98% identical to the full-length amino acid sequence as set forth in SEQ ID NO: 2. Some embodiments relate to immunogenic proteins that have an amino acid sequence that is 99% identical to the full-length amino acid sequence as set forth in SEQ ID NO: 2. In some embodiments, the protein is free of a leader sequence. In some embodiments, the protein is free of an IgE leader sequence.

Fragments of proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a protein. Immunogenic fragments of SEQ ID NO: 2 can be provided. Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO: 2. In some embodiments, fragments include a leader sequence, such as for example, an immunoglobulin leader, such as the IgE leader. In some embodiments, fragments are free of a leader sequence. In some embodiments, fragments are free of a leader sequence, such as for example, an IgE leader sequence.

Immunogenic fragments of proteins with amino acid sequences homologous to immunogenic fragments of SEQ ID NO: 2 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO: 2. Some embodiments relate to immunogenic fragments that have 96% homology to the immunogenic fragments of protein sequences herein. Some embodiments relate to immunogenic fragments that have 97% homology to the immunogenic fragments of protein sequences herein. Some embodiments relate to immunogenic fragments that have 98% homology to the immunogenic fragments of protein sequences herein. Some embodiments relate to immunogenic fragments that have 99% homology to the immunogenic fragments of protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO: 2 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO: 2. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence that encodes the protein without a signal peptide coding sequences.

Fragments of SEQ ID NO: 1 may comprise 30 or more nucleotides, including preferably sequences that encode an immunodominant epitope. In some embodiments, fragments of SEQ ID NO: 1 may comprise 45 or more nucleotides, including preferably sequences that encode an immunodominant epitope. In some embodiments, fragments of SEQ ID NO: 1 may comprise 60 or more nucleotides, including preferably sequences that encode an immunodominant epitope. In some embodiments, fragments of SEQ ID NO: 1 may comprise 75 or more nucleotides, including preferably sequences that encode an immunodominant epitope. In some embodiments, fragments of SEQ ID NO: 1 may comprise 90 or more nucleotides, including preferably sequences that encode an immunodominant epitope. In some embodiments, fragments of SEQ ID NO: 1 may comprise 120 or more nucleotides, including preferably sequences that encode an immunodominant epitope. In some embodiments, fragments of SEQ ID NO: 1 may comprise 150 or more nucleotides, including preferably sequences that encode an immunodominant epitope. In some embodiments, fragments of SEQ ID NO: 1 may comprise 180 or more nucleotides, including preferably sequences that encode an immunodominant epitope. In some embodiments, fragments of SEQ ID NO: 1 may comprise 210 or more nucleotides, including preferably sequences that encode an immunodominant epitope. In some embodiments, fragments of SEQ ID NO: 1 may comprise 240 or more nucleotides, including preferably sequences that encode an immunodominant epitope. In some embodiments, fragments of SEQ ID NO: 1 may comprise 270 or more nucleotides, including preferably sequences that encode an immunodominant epitope. In some embodiments, fragments of SEQ ID NO: 1 may comprise 300 or more nucleotides, including preferably sequences that encode an immunodominant epitope. In some embodiments, fragments of SEQ ID NO: 1 may comprise 360 or more nucleotides, including preferably sequences that encode an immunodominant epitope. In some embodiments, fragments of SEQ ID NO: 1 may comprise 420 or more nucleotides, including preferably sequences that encode an immunodominant epitope. In some embodiments, fragments of SEQ ID NO: 1 may comprise 480 or more nucleotides, including preferably sequences that encode an immunodominant epitope. In some embodiments, fragments of SEQ ID NO: 1 may comprise 540 or more nucleotides, including preferably sequences that encode an immunodominant epitope. In some embodiments, fragments of SEQ ID NO: 1 may comprise 600 or more nucleotides, including preferably sequences that encode an immunodominant epitope. In some embodiments, fragments of SEQ ID NO: 1 may comprise 300 or more nucleotides, including preferably sequences that encode an immunodominant epitope. In some embodiments, fragments of SEQ ID NO: 1 may comprise 660 or more nucleotides, including preferably sequences that encode an immunodominant epitope. In some embodiments, fragments of SEQ ID NO: 1 may comprise 720 or more nucleotides, including preferably sequences that encode an immunodominant epitope. In some embodiments, fragments of SEQ ID NO: 1 may comprise 780 or more nucleotides, including preferably sequences that encode an immunodominant epitope. In some embodiments, fragments of SEQ ID NO: 1 may comprise 840 or more nucleotides, including preferably sequences that encode an immunodominant epitope. In some embodiments, fragments of SEQ ID NO: 1 may comprise 900 or more nucleotides, including preferably sequences that encode an immunodominant epitope. In some embodiments, fragments of SEQ ID NO: 1 may comprise 960 or more nucleotides, including preferably sequences that encode an immunodominant epitope. In some embodiments, fragments of SEQ ID NO: 1 may comprise 1020 or more nucleotides, including preferably sequences that encode an immunodominant epitope. In some embodiments, fragments of SEQ ID NO: 1 may comprise 1080 or more nucleotides, including preferably sequences that encode an immunodominant epitope. In some embodiments, fragments of SEQ ID NO: 1 may comprise 1140 or more nucleotides, including preferably sequences that encode an immunodominant epitope. In some embodiments, fragments of SEQ ID NO: 1 may comprise 1200 or more nucleotides, including preferably sequences that encode an immunodominant epitope. In some embodiments, fragments of SEQ ID NO: 1 may comprise 1260 or more nucleotides, including preferably sequences that encode an immunodominant epitope. In some embodiments, fragments of SEQ ID NO: 1 may comprise 1320 or more nucleotides, including preferably sequences that encode an immunodominant epitope. In some embodiments, fragments of SEQ ID NO: 1 may comprise 1380 or more nucleotides, including preferably sequences that encode an immunodominant epitope. In some embodiments, fragments of SEQ ID NO: 1 may comprise 1440 or more nucleotides, including preferably sequences that encode an immunodominant epitope. In some embodiments, fragments of SEQ ID NO: 1 may comprise 1500 or more nucleotides, including preferably sequences that encode an immunodominant epitope. In some embodiments, fragments of SEQ ID NO: 1 may comprise 1560 or more nucleotides, including preferably sequences that encode an immunodominant epitope. In some embodiments, fragments of SEQ ID NO: 1 may comprise 1620 or more nucleotides, including preferably sequences that encode an immunodominant epitope. In some embodiments, fragments of SEQ ID NO: 1 may comprise 1680 or more nucleotides, including preferably sequences that encode an immunodominant epitope. In some embodiments, fragments of SEQ ID NO: 1 may comprise 1740 or more nucleotides, including preferably sequences that encode an immunodominant epitope. In some embodiments, fragments of SEQ ID NO: 1 may comprise 1800 or more nucleotides, including preferably sequences that encode an immunodominant epitope. In some embodiments, fragments of SEQ ID NO: 1 may comprise 1860 or more nucleotides, including preferably sequences that encode an immunodominant epitope. In some embodiments, fragments of SEQ ID NO: 1 may comprise 1920 or more nucleotides, including preferably sequences that encode an immunodominant epitope. In some embodiments, fragments of SEQ ID NO: 1 may comprise 1980 or more nucleotides, including preferably sequences that encode an immunodominant epitope. In some embodiments, fragments of SEQ ID NO: 1 may comprise 2040 or more nucleotides, including preferably sequences that encode an immunodominant epitope. In some embodiments, fragments of SEQ ID NO: 1 may comprise 2100 or more nucleotides, including preferably sequences that encode an immunodominant epitope. In some embodiments, fragments of SEQ ID NO: 1 may comprise 2160 or more nucleotides, including preferably sequences that encode an immunodominant epitope. In some embodiments, fragments of SEQ ID NO: 1 may comprise 2220 or more nucleotides, including preferably sequences that encode an immunodominant epitope. In some embodiments, fragments of SEQ ID NO: 1 may comprise 2280 or more nucleotides, including preferably sequences that encode an immunodominant epitope. In some embodiments, fragments of SEQ ID NO: 1 may comprise 2340 or more nucleotides, including preferably sequences that encode an immunodominant epitope. In some embodiments, fragments of SEQ ID NO: 1 may comprise 2400 or more nucleotides, including preferably sequences that encode an immunodominant epitope. In some embodiments, fragments of SEQ ID NO: 1 may comprise 2460 or more nucleotides, including preferably sequences that encode an immunodominant epitope. In some embodiments, fragments of SEQ ID NO: 1 may comprise 2520 or more nucleotides, including preferably sequences that encode an immunodominant epitope. In some embodiments, fragments of SEQ ID NO: 1 may comprise 2580 or more nucleotides, including preferably sequences that encode an immunodominant epitope. In some embodiments, fragments of SEQ ID NO: 1 may comprise 2640 or more nucleotides, including preferably sequences that encode an immunodominant epitope. In some embodiments, fragments of SEQ ID NO: 1 may comprise 2700 or more nucleotides, including preferably sequences that encode an immunodominant epitope. In some embodiments, fragments of SEQ ID NO: 1 may comprise 2760 or more nucleotides, including preferably sequences that encode an immunodominant epitope. In some embodiments, fragments of SEQ ID NO: 1 may comprise 2820 or more nucleotides, including preferably sequences that encode an immunodominant epitope. In some embodiments, fragments of SEQ ID NO: 1 may comprise 2880 or more nucleotides, including preferably sequences that encode an immunodominant epitope. In some embodiments, fragments of SEQ ID NO: 1 may comprise 2940 or more nucleotides, including preferably sequences that encode an immunodominant epitope. In some embodiments, fragments of SEQ ID NO: 1 may comprise 3000 or more nucleotides, including preferably sequences that encode an immunodominant epitope. In some embodiments, fragments of SEQ ID NO: 1 may comprise 3060 or more nucleotides, including preferably sequences that encode an immunodominant epitope. In some embodiments, fragments of SEQ ID NO: 1 may comprise 3120 or more nucleotides, including preferably sequences that encode an immunodominant epitope. In some embodiments, fragments of SEQ ID NO: 1 may comprise 3180 or more nucleotides, including preferably sequences that encode an immunodominant epitope. In some embodiments, fragments of SEQ ID NO: 1 may comprise 3240 or more nucleotides, including preferably sequences that encode an immunodominant epitope. In some embodiments, fragments of SEQ ID NO: 1 may comprise 3300 or more nucleotides, including preferably sequences that encode an immunodominant epitope. In some embodiments, fragments of SEQ ID NO: 1 may comprise 3360 or more nucleotides, including preferably sequences that encode an immunodominant epitope. In some embodiments, fragments of SEQ ID NO: 1 may comprise 3420 or more nucleotides, including preferably sequences that encode an immunodominant epitope. In some embodiments, fragments of SEQ ID NO: 1 may comprise 3480 or more nucleotides, including preferably sequences that encode an immunodominant epitope. In some embodiments, fragments of SEQ ID NO: 1 may comprise coding sequences for the IgE leader sequences. In some embodiments, fragments of SEQ ID NO: 1 do not comprise coding sequences for the IgE leader sequences.

Fragments may comprise fewer than 30 nucleotides, in some embodiments fewer than 40 nucleotides, in some embodiments fewer than 50 nucleotides, in some embodiments fewer than 60 nucleotides, in some embodiments fewer than 75 nucleotides, in some embodiments fewer than 90 nucleotides, in some embodiments fewer than 120 nucleotides, in some embodiments fewer than 150 nucleotides, in some embodiments fewer than 180 nucleotides, in some embodiments fewer than 210 nucleotides, in some embodiments fewer than 240 nucleotides, in some embodiments fewer than 270 nucleotides, in some embodiments fewer than 300 nucleotides, in some embodiments fewer than 360 nucleotides, in some embodiments fewer than 420 nucleotides, in some embodiments fewer than 480 nucleotides, in some embodiments fewer than 540 nucleotides, in some embodiments fewer than 600 nucleotides, in some embodiments fewer than 660 nucleotides, in some embodiments fewer than 720 nucleotides, in some embodiments fewer than 780 nucleotides, in some embodiments fewer than 840 nucleotides, in some embodiments fewer than 900 nucleotides, in some embodiments fewer than 960 nucleotides, in some embodiments fewer than 1020 nucleotides, in some embodiments fewer than 1080 nucleotides, in some embodiments fewer than 1140 nucleotides, in some embodiments fewer than 1200 nucleotides, in some embodiments fewer than 1260 nucleotides, in some embodiments fewer than 1320 nucleotides, in some embodiments fewer than 1380 nucleotides, in some embodiments fewer than 1440 nucleotides, in some embodiments fewer than 1500 nucleotides, in some embodiments fewer than 1560 nucleotides, in some embodiments fewer than 1620 nucleotides, in some embodiments fewer than 1680 nucleotides, in some embodiments fewer than 1740 nucleotides, in some embodiments fewer than 1800 nucleotides, in some embodiments fewer than 1860 nucleotides, in some embodiments fewer than 1920 nucleotides, in some embodiments fewer than 1980 nucleotides, in some embodiments fewer than 2040 nucleotides, in some embodiments fewer than 2100 nucleotides, in some embodiments fewer than 2160 nucleotides, in some embodiments fewer than 2220 nucleotides, in some embodiments fewer than 2280 nucleotides, in some embodiments fewer than 2340 nucleotides, in some embodiments fewer than 2400 nucleotides, in some embodiments fewer than 2460 nucleotides, in some embodiments fewer than 2520 nucleotides, in some embodiments fewer than 2580 nucleotides, in some embodiments fewer than 2640 nucleotides, in some embodiments fewer than 2700 nucleotides, in some embodiments fewer than 2760 nucleotides, in some embodiments fewer than 2820 nucleotides, in some embodiments fewer than 2860 nucleotides, in some embodiments fewer than 2940 nucleotides, in some embodiments fewer than 3000 nucleotides, in some embodiments fewer than 3060 nucleotides, in some embodiments fewer than 3120 nucleotides, in some embodiments fewer than 3180 nucleotides, in some embodiments fewer than 3240 nucleotides, in some embodiments fewer than 3300 nucleotides, in some embodiments fewer than 3360 nucleotides, in some embodiments fewer than 3420 nucleotides, in some embodiments fewer than 3480 nucleotides, and in some embodiments fewer than 3510 nucleotides.

Fragments of SEQ ID NO: 2 may comprise 10 or more amino acids, including preferably sequences that encode an immunodominant epitope. In some embodiments, fragments of SEQ ID NO: 2 may comprise 15 or more amino acids, including preferably sequences that encode an immunodominant epitope. In some embodiments, fragments of SEQ ID NO: 2 or SEQ ID NO:5 may comprise 20 or more amino acids, including preferably sequences that encode an immunodominant epitope. In some embodiments, fragments of SEQ ID NO: 2 may comprise 25 or more amino acids, including preferably sequences that encode an immunodominant epitope. In some embodiments, fragments of SEQ ID NO: 2 may comprise 30 or more amino acids, including preferably sequences that encode an immunodominant epitope. In some embodiments, fragments of SEQ ID NO: 2 may comprise 35 or more amino acids, including preferably sequences that encode an immunodominant epitope. In some embodiments, fragments of SEQ ID NO: 2 may comprise 40 or more amino acids, including preferably sequences that encode an immunodominant epitope. In some embodiments, fragments of SEQ ID NO: 2 may comprise 45 or more amino acids, including preferably sequences that encode an immunodominant epitope. In some embodiments, fragments of SEQ ID NO: 2 may comprise 50 or more amino acids, including preferably sequences that encode an immunodominant epitope. In some embodiments, fragments of SEQ ID NO: 2 may comprise 60 or more amino acids, including preferably sequences that encode an immunodominant epitope. In some embodiments, fragments of SEQ ID NO: 2 may comprise 65 or more amino acids, including preferably sequences that encode an immunodominant epitope. In some embodiments, fragments of SEQ ID NO: 2 may comprise 70 or more amino acids, including preferably sequences that encode an immunodominant epitope. In some embodiments, fragments of SEQ ID NO: 2 may comprise 90 or more amino acids, including preferably sequences that encode an immunodominant epitope. In some embodiments, fragments of SEQ ID NO: 2 may comprise 120 or more amino acids, including preferably sequences that encode an immunodominant epitope. In some embodiments, fragments of SEQ ID NO: 2 may comprise 150 or more amino acids, including preferably sequences that encode an immunodominant epitope. In some embodiments, fragments of SEQ ID NO: 2 may comprise 180 or more amino acids, including preferably sequences that encode an immunodominant epitope. In some embodiments, fragments of SEQ ID NO: 2 may comprise 210 or more amino acids, including preferably sequences that encode an immunodominant epitope. In some embodiments, fragments of SEQ ID NO: 2 may comprise 240 or more amino acids, including preferably sequences that encode an immunodominant epitope. In some embodiments, fragments of SEQ ID NO: 2 may comprise 270 or more amino acids, including preferably sequences that encode an immunodominant epitope. In some embodiments, fragments of SEQ ID NO: 2 may comprise 300 or more amino acids, including preferably sequences that encode an immunodominant epitope. In some embodiments, fragments of SEQ ID NO: 2 may comprise 330 or more amino acids, including preferably sequences that encode an immunodominant epitope. In some embodiments, fragments of SEQ ID NO: 2 may comprise 360 or more amino acids, including preferably sequences that encode an immunodominant epitope. In some embodiments, fragments of SEQ ID NO: 2 may comprise 390 or more amino acids, including preferably sequences that encode an immunodominant epitope. In some embodiments, fragments of SEQ ID NO: 2 may comprise 420 or more amino acids, including preferably sequences that encode an immunodominant epitope. In some embodiments, fragments of SEQ ID NO: 2 may comprise 450 or more amino acids, including preferably sequences that encode an immunodominant epitope. In some embodiments, fragments of SEQ ID NO: 2 may comprise 480 or more amino acids, including preferably sequences that encode an immunodominant epitope. In some embodiments, fragments of SEQ ID NO: 2 may comprise 510 or more amino acids, including preferably sequences that encode an immunodominant epitope. In some embodiments, fragments of SEQ ID NO: 2 may comprise 540 or more amino acids, including preferably sequences that encode an immunodominant epitope. In some embodiments, fragments of SEQ ID NO: 2 may comprise 570 or more amino acids, including preferably sequences that encode an immunodominant epitope. In some embodiments, fragments of SEQ ID NO: 2 may comprise 600 or more amino acids, including preferably sequences that encode an immunodominant epitope. In some embodiments, fragments of SEQ ID NO: 2 may comprise 630 or more amino acids, including preferably sequences that encode an immunodominant epitope. In some embodiments, fragments of SEQ ID NO: 2 may comprise 660 or more amino acids, including preferably sequences that encode an immunodominant epitope. In some embodiments, fragments of SEQ ID NO: 2 may comprise 690 or more amino acids, including preferably sequences that encode an immunodominant epitope. In some embodiments, fragments of SEQ ID NO: 2 may comprise 720 or more amino acids, including preferably sequences that encode an immunodominant epitope. In some embodiments, fragments of SEQ ID NO: 2 may comprise 750 or more amino acids, including preferably sequences that encode an immunodominant epitope. In some embodiments, fragments of SEQ ID NO: 2 may comprise 780 or more amino acids, including preferably sequences that encode an immunodominant epitope. In some embodiments, fragments of SEQ ID NO: 2 may comprise 810 or more amino acids, including preferably sequences that encode an immunodominant epitope. In some embodiments, fragments of SEQ ID NO: 2 may comprise 840 or more amino acids, including preferably sequences that encode an immunodominant epitope. In some embodiments, fragments of SEQ ID NO: 2 may comprise 870 or more amino acids, including preferably sequences that encode an immunodominant epitope. In some embodiments, fragments of SEQ ID NO: 2 may comprise 900 or more amino acids, including preferably sequences that encode an immunodominant epitope. In some embodiments, fragments of SEQ ID NO: 2 may comprise 930 or more amino acids, including preferably sequences that encode an immunodominant epitope. In some embodiments, fragments of SEQ ID NO: 2 may comprise 960 or more amino acids, including preferably sequences that encode an immunodominant epitope. In some embodiments, fragments of SEQ ID NO: 2 may comprise 990 or more amino acids, including preferably sequences that encode an immunodominant epitope. In some embodiments, fragments of SEQ ID NO: 2 may comprise 1020 or more amino acids, including preferably sequences that encode an immunodominant epitope. In some embodiments, fragments of SEQ ID NO: 2 may comprise 1050 or more amino acids, including preferably sequences that encode an immunodominant epitope. In some embodiments, fragments of SEQ ID NO: 2 may comprise 1080 or more amino acids, including preferably sequences that encode an immunodominant epitope. In some embodiments, fragments of SEQ ID NO: 2 may comprise coding sequences for the IgE leader sequences. In some embodiments, fragments of SEQ ID NO: 2 do not comprise coding sequences for the IgE leader sequences.

Fragments may comprise fewer than 15 amino acids, in some embodiments fewer than 20 amino acids, in some embodiments fewer than 24 amino acids, in some embodiments fewer than 30 amino acids, in some embodiments fewer than 36 amino acids, in some embodiments fewer than 42 amino acids, in some embodiments fewer than 48 amino acids, in some embodiments fewer than 54 amino acids, in some embodiments fewer than 60 amino acids, in some embodiments fewer than 72 amino acids, in some embodiments fewer than 90 amino acids, in some embodiments fewer than 120 amino acids, in some embodiments fewer than 150 amino acids, in some embodiments fewer than 180 amino acids, in some embodiments fewer than 210 amino acids in some embodiments fewer than 240 amino acids, in some embodiments fewer than 260 amino acids, in some embodiments fewer than 290 amino acids, in some embodiments fewer than 320 amino acids, in some embodiments fewer than 350 amino acids, in some embodiments fewer than 380 amino acids, in some embodiments fewer than 410 amino acids in some embodiments fewer than 440 amino acids, in some embodiments fewer than 470 amino acids in some embodiments fewer than 500 amino acids, in some embodiments fewer than 530 amino acids in some embodiments fewer than 560 amino acids, in some embodiments fewer than 590 amino acids, in some embodiments fewer than 620 amino acids, in some embodiments fewer than 650 amino acids, in some embodiments fewer than 680 amino acids, in some embodiments fewer than 710 amino acids, in some embodiments fewer than 740 amino acids, in some embodiments fewer than 770 amino acids, in some embodiments fewer than 800 amino acids, in some embodiments fewer than 830 amino acids, in some embodiments fewer than 860 amino acids, in some embodiments fewer than 890 amino acids, in some embodiments fewer than 920 amino acids, in some embodiments fewer than 950 amino acids, in some embodiments fewer than 980 amino acids, in some embodiments fewer than 1010 amino acids, in some embodiments fewer than 1040 amino acids, in some embodiments fewer than 1070 amino acids, in some embodiments fewer than 1200 amino acids, in some embodiments fewer than 1230 amino acids, in some embodiments fewer than 1260 amino acids, in some embodiments fewer than 1290 amino acids, in some embodiments fewer than 1320 amino acids, in some embodiments fewer than 1350 amino acids, in some embodiments fewer than 1380 amino acids, in some embodiments fewer than 1410 amino acids, in some embodiments fewer than 1440 amino acids, in some embodiments fewer than 1470 amino acids, and in some embodiments fewer than 1500 amino acids.

b. Additional Cancer Antigens

The inventive vaccine can comprise or encode one or more cancer antigens in addition to the dTERT antigen described above. In this regard, the one or more additional cancer antigens can be a nucleic acid sequence, an amino acid sequence, or a combination thereof. The nucleic acid sequence can be DNA, RNA, cDNA, a variant thereof, a fragment thereof, or a combination thereof. The nucleic acid sequence can also include additional sequences that encode linker or tag sequences that are linked to the cancer antigen by a peptide bond. The amino acid sequence can be a protein, a peptide, a variant thereof, a fragment thereof, or a combination thereof. The one or more additional cancer antigen can be a recombinant cancer antigen.

3. Vaccine in Combination with Immune Checkpoint Inhibitor

An inhibitor of an immune checkpoint molecule can be a nucleic acid sequence, an amino acid sequence, a small molecule, or a combination thereof. The nucleic acid sequence can be DNA, RNA, cDNA, a variant thereof, a fragment thereof, or a combination thereof. The nucleic acid can also include additional sequences that encode linker or tag sequences that are linked to the immune checkpoint inhibitor by a peptide bond. The small molecule may be a low molecular weight, for example, less than 800 Daltons, organic or inorganic compound that can serve as an enzyme substrate, ligand (or analog thereof) bound by a protein or nucleic acid, or regulator of a biological process. The amino acid sequence can be protein, a peptide, a variant thereof, a fragment thereof, or a combination thereof.

In some embodiments, the immune checkpoint inhibitor can be one or more nucleic acid sequences encoding an antibody, a variant thereof, a fragment thereof, or a combination thereof. In other embodiments, the immune checkpoint inhibitor can be an antibody, a variant thereof, a fragment thereof, or a combination thereof.

4. Vaccine Constructs and Plasmids

The inventive vaccine can comprise nucleic acid constructs or plasmids that encode the above described antigens and/or antibodies. The nucleic acid constructs or plasmids can include or contain one or more heterologous nucleic acid sequences. Provided herein are genetic constructs that can comprise a nucleic acid sequence that encodes the above described antigens and/or antibodies. The genetic construct can be present in the cell as a functioning extrachromosomal molecule. The genetic construct can be a linear minichromosome including centromere, telomeres or plasmids or cosmids. The genetic constructs can include or contain one or more heterologous nucleic acid sequences.

The genetic constructs can be in the form of plasmids expressing the above described antigens and/or antibodies in any order.

The genetic construct can also be part of a genome of a recombinant viral vector, including recombinant adenovirus, recombinant adenovirus-associated virus (AAV) and recombinant vaccinia virus. The genetic construct can be part of the genetic material in attenuated live microorganisms or recombinant microbial vectors which live in cells.

The genetic constructs can comprise regulatory elements for gene expression of the coding sequences of the nucleic acid. The regulatory elements can be a promoter, an enhancer, an initiation codon, a stop codon, or a polyadenylation signal.

The nucleic acid sequences can make up a genetic construct that can be a vector. The vector can be capable of expressing the above described antigens and/or antibodies in the cell of a mammal in a quantity effective to elicit an immune response in the mammal. The vector can be recombinant. The vector can comprise one or more heterologous nucleic acid molecules encoding the above described antigens and/or antibodies. The vector can be a plasmid. The vector can be useful for transfecting host cells with one or more nucleic acid molecules encoding the above described antigens and/or antibodies, wherein the transfected host cells are cultured and maintained under conditions wherein the above described antigens and/or antibodies are expressed.

Coding sequences can be optimized for stability and high levels of expression. In some instances, codons are selected to reduce secondary structure formation in the RNA, such as that formed due to intramolecular bonding.

The vector can comprise one or more heterologous nucleic acid molecules encoding the above described antigens and/or antibodies and can further comprise an initiation codon, which can be upstream of the one or more cancer antigen coding sequence(s), and a stop codon, which can be downstream of the coding sequence(s) of the above described antigens and/or antibodies. The initiation and termination codon can be in frame with the coding sequence(s) of the above described antigens and/or antibodies. The vector can also comprise a promoter that is operably linked to the coding sequence(s) of the above described antigens and/or antibodies. The promoter operably linked to the coding sequence(s) of the above described antigens and/or antibodies can be any suitable protein, including, but not limited to, a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter also can be a promoter from a mammalian promoter, such as, for example, an actin promoter, a myosin promoter, a hemoglobin promoter, a muscle creatine promoter, or a metallothionein promoter. The promoter also can be a tissue-specific promoter, such as a muscle- or skin-specific promoter that is natural or synthetic (see, e.g., U.S. Patent Application Publication US 2004/0175727).

The vector also can comprise a polyadenylation signal, which can be downstream of the coding sequence(s) of the above described antigens and/or antibodies. The polyadenylation signal can be any suitable polyadenylation signal, including, for example, a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal can be a polyadenylation signal from a pCEP4 vector (Invitrogen, San Diego, Calif.).

The vector also can comprise an enhancer upstream of the above described antigens and/or antibodies. The enhancer can be necessary for DNA expression. The enhancer can be isolated or derived from any suitable mammalian gene, such as, for example actin, myosin, hemoglobin, muscle creatine, or virus, such as, for example, CMV, HA, RSV or EBV. Polynucleotide function enhancers are described in, for example, U.S. Pat. Nos. 5,593,972 and 5,962,428, and International Patent Application Publication WO 94/016737.

The vector also can comprise a mammalian origin of replication in order to maintain the vector extrachromosomally and produce multiple copies of the vector in a cell. The vector can be pVAX1, pCEP4 or pREP4 from Invitrogen (San Diego, Calif.), which can comprise the Epstein Barr virus origin of replication and nuclear antigen EBNA-1 coding region, which can produce high copy episomal replication without integration. The vector can be pVAX1 or a variant thereof. For example, the pVAX1 variant plasmid pGX0001 is a 2998 base pair variant of the backbone vector plasmid pVAX1 (Invitrogen, Carlsbad Calif.). The pGX0001 plasmid comprises the following elements: (a) the CMV promoter located at bases 137-724, (b) the T7 promoter/priming site located at bases 664-683, (c) multiple cloning sites located at bases 696-811, (d) bovine GH polyadenylation signal located at bases 829-1053, (e) the kanamycin resistance ($Kan^R$) gene located at bases 1226-2020, and (0 the pUC origin located at bases 2320-2993.

Based upon the sequence of pVAX1 available from Invitrogen, additional mutations can be made to pVAX1 in order to generate the inventive vaccine. In one embodiment, following mutations can be made in the nucleic acid sequence of pVAX1:

C>G241 in CMV promoter

C>T 1158 backbone, downstream of the bovine growth hormone polyadenylation signal (bGH polyA)

A>—2092 backbone, downstream of the Kanamycin resistance gene (Kan$^{R}$)

C>T 2493 in pUC origin of replication (pUC ori)

G>C 2969 in very end of pUC Ori upstream of RNASeH site, and base pairs 2, 3 and 4 can be changed from ACT to CTG in backbone, upstream of CMV promoter.

The vector also can comprise a regulatory sequence, which can be well-suited for gene expression in a mammalian (e.g., canine) cell into which the vector is administered. The one or more cancer antigen sequences disclosed herein can comprise one or more codons that allow more efficient transcription of the coding sequence in a particular host cell.

The vector can be pSE420 (Invitrogen, San Diego, Calif.), which can be used for protein production in *Escherichia coli* (*E. coli*). The vector can also be pYES2 (Invitrogen, San Diego, Calif.), which can be used for protein production in *Saccharomyces cerevisiae* strains of yeast. The vector can also be of the MAXBAC™ complete baculovirus expression system (Invitrogen, San Diego, Calif.), which can be used for protein production in insect cells. The vector can also be pcDNA I or pcDNA3 (Invitrogen, San Diego, Calif.), which may be used for protein production in mammalian cells such as Chinese hamster ovary (CHO) cells. The vector can be produced using routine techniques and readily available starting materials, such as those described in, for example, Sambrook et al., Molecular Cloning and Laboratory Manual, Second Ed., Cold Spring Harbor (1989).

In one embodiment, the inventive vaccine is a plasmid vector, which comprises the polynucleotide sequence of SEQ ID NO: 3.

5. Pharmaceutical Compositions of the Vaccine

The vaccine can be in the form of a pharmaceutical composition, i.e., a composition comprising the vaccine and a pharmaceutically acceptable carrier. The pharmaceutical composition can comprise the vaccine. The pharmaceutical compositions can comprise about 5 nanograms to about 10 mg of the DNA of the vaccine. In some embodiments, pharmaceutical compositions according to the present invention comprise about 25 nanograms to about 5 mg of DNA of the vaccine. In some embodiments, the pharmaceutical compositions contain about 50 nanograms to about 1 mg of DNA of the vaccine. In some embodiments, the pharmaceutical compositions contain about 0.1 to about 1,500 micrograms of DNA of the vaccine. In some embodiments, the pharmaceutical compositions contain about 1 to about 800 micrograms of DNA of the vaccine. In some embodiments, the pharmaceutical compositions contain about 5 to about 500 micrograms of DNA of the vaccine. In some embodiments, the pharmaceutical compositions contain about 10 to about 250 micrograms of DNA of the vaccine. In some embodiments, the pharmaceutical compositions contain about 15 to about 150 micrograms of DNA of the vaccine. In some embodiments, the pharmaceutical compositions contain about 20 to about 100 micrograms of DNA of the vaccine. In some embodiments, the pharmaceutical compositions contain about 25 to about 75 micrograms of DNA of the vaccine. In some embodiments, the pharmaceutical compositions contain about 30 to about 50 micrograms of DNA of the vaccine. In some embodiments, the pharmaceutical compositions contain about 35 to about 40 micrograms of DNA of the vaccine. In some embodiments, the pharmaceutical compositions contain about 100 to about 200 microgram DNA of the vaccine. In some embodiments, the pharmaceutical compositions comprise about 10 microgram to about 100 micrograms of DNA of the vaccine. In some embodiments, the pharmaceutical compositions comprise about 20 micrograms to about 80 micrograms of DNA of the vaccine. In some embodiments, the pharmaceutical compositions comprise about 25 micrograms to about 60 micrograms of DNA of the vaccine. In some embodiments, the pharmaceutical compositions comprise about 30 nanograms to about 50 micrograms of DNA of the vaccine. In some embodiments, the pharmaceutical compositions comprise about 35 nanograms to about 45 micrograms of DNA of the vaccine. In some preferred embodiments, the pharmaceutical compositions contain about 0.1 to about 800 micrograms of DNA of the vaccine. In some preferred embodiments, the pharmaceutical compositions contain about 1 to about 500 micrograms of DNA of the vaccine. In some preferred embodiments, the pharmaceutical compositions contain about 25 to about 300 micrograms of DNA of the vaccine. In some preferred embodiments, the pharmaceutical compositions contain about 100 to about 200 microgram DNA of the vaccine.

In some embodiments, pharmaceutical compositions according to the present invention comprise at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995, 1000, 1005, 1010, 1015, 1020, 1025, 1030, 1035, 1040, 1045, 1050, 1055, 1060, 1065, 1070, 1075, 1080, 1085, 1090, 1095, 1100, 1105, 1110, 1115, 1120, 1125, 1130, 1135, 1140, 1145, 1150, 1155, 1160, 1165, 1170, 1175, 1180, 1185, 1190, 1195, 1200, 1205, 1210, 1215, 1220, 1225, 1230, 1235, 1240, 1245, 1250, 1255, 1260, 1265, 1270, 1275, 1280, 1285, 1290, 1295, 1300, 1305, 1310, 1315, 1320, 1325, 1330, 1335, 1340, 1345, 1350, 1355, 1360, 1365, 1370, 1375, 1380, 1385, 1390, 1395, 1400, 1405, 1410, 1415, 1420, 1425, 1430, 1435, 1440, 1445, 1450, 1455, 1460, 1465, 1470, 1475, 1480, 1485, 1490, 1495, 1500, 1505, 1510, 1515, 1520, 1525, 1530, 1535, 1540, 1545, 1550, 1555, 1560, 1565, 1570, 1575, 1580, 1585, 1590, 1595, 1600, 1605, 1610, 1615, 1620, 1625, 1630, 1635, 1640, 1645, 1650, 1655, 1660, 1665, 1670, 1675, 1680, 1685, 1690, 1695, 1700, 1705, 1710, 1715, 1720, 1725, 1730, 1735, 1740, 1745, 1750, 1755, 1760, 1765, 1770, 1775, 1780, 1785, 1790, 1795, or 1800 micrograms of DNA of the vaccine.

In other embodiments, the pharmaceutical composition can comprise up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995, 1000, 1005, 1010, 1015, 1020, 1025, 1030, 1035, 1040, 1045, 1050, 1055, 1060, 1065, 1070, 1075, 1080, 1085, 1090, 1095, 1100, 1105, 1110, 1115, 1120, 1125, 1130, 1135, 1140, 1145, 1150, 1155, 1160, 1165, 1170, 1175, 1180, 1185, 1190, 1195, 1200, 1205, 1210, 1215, 1220, 1225, 1230, 1235, 1240, 1245, 1250, 1255, 1260, 1265, 1270, 1275, 1280, 1285, 1290, 1295, 1300, 1305, 1310, 1315, 1320, 1325, 1330, 1335, 1340, 1345, 1350, 1355, 1360, 1365, 1370, 1375, 1380, 1385, 1390, 1395, 1400, 1405, 1410, 1415, 1420, 1425, 1430, 1435, 1440, 1445, 1450, 1455, 1460, 1465, 1470, 1475, 1480, 1485, 1490, 1495, 1500, 1505, 1510, 1515, 1520, 1525, 1530, 1535, 1540, 1545, 1550, 1555, 1560, 1565, 1570, 1575, 1580, 1585, 1590, 1595, 1600, 1605, 1610, 1615, 1620, 1625, 1630, 1635, 1640, 1645, 1650, 1655, 1660, 1665, 1670, 1675, 1680, 1685, 1690, 1695, 1700, 1705, 1710, 1715, 1720, 1725, 1730, 1735, 1740, 1745, 1750, 1755, 1760, 1765, 1770, 1775, 1780, 1785, 1790, 1795, or 1800 micrograms of DNA of the vaccine.

The pharmaceutical composition can further comprise other agents for formulation purposes according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

The vaccine or pharmaceutical composition can further comprise a pharmaceutically acceptable carrier or excipient. The pharmaceutically acceptable carrier or excipient can be functional molecules as vehicles, adjuvants, carriers, or diluents. The pharmaceutically acceptable carrier or excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent can be a polyanion, polycation, including poly-L-glutamate (LGS), or lipid. The transfection facilitating agent can be poly-L-glutamate, and more preferably, the poly-L-glutamate can be present in the vaccine at a concentration less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid. In some embodiments, the vaccine composition can also include one or more transfection facilitating agents, such as, for example, lipids, liposomes (e.g., lecithin liposomes or other liposomes known in the art) as a DNA-liposome mixture (see, e.g., International Patent Application Publication WO 93/24640), calcium ions, viral proteins, polyanions, polycations, or nanoparticles, or other known transfection facilitating agents. Preferably, the transfection facilitating agent can be a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable carrier or excipient can be an adjuvant. The adjuvant can be other genes that are expressed in alternative plasmid or are delivered as proteins in combination with the plasmid above in the vaccine. The adjuvant can be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof. In an exemplary embodiment, the adjuvant is IL-12.

Other genes which can be useful adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, pl50.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2, and functional fragments thereof.

6. Vaccines for Treating Particular Cancers

The inventive vaccine can comprise a polynucleotide sequence encoding a dTERT antigen as the only cancer antigen to treat particular cancer or tumor in a mammal. Alternatively, the inventive vaccine can comprise one or more additional polynucleotide sequences that encode one or more additional cancer antigens to treat a particular cancer or tumor in a mammal (e.g., a canine). In another embodiment, the inventive vaccine comprising a polynucleotide encoding a dTERT antigen can be administered to a mammal in combination with one or more separate vaccines, each of which encode or comprise one more additional cancer antigens, such as those described herein, to treat a particular cancer or tumor in a mammal.

Depending upon whether the inventive method of treating a cancer or tumor targets a TERT antigen alone, or a TERT antigen in combination with one or more additional cancer antigens, various cancers or other tumor types may be targeted with the vaccine. Such cancers include, for example, can include melanoma, prostate cancer, liver cancer, cervical cancer, recurrent respiratory papillomatosis (RRP), anal cancer, head and neck cancer, blood cancers (e.g., leukemia, lymphoma, myeloma), lung carcinomas (e.g., non-small cell lung carcinoma), esophageal squamous cell carcinomas, bladder cancer, colorectal cancer, gastric cancer, hepatocarcinoma, brain cancer (e.g., glioblastoma), pancreatic cancer, synovial carcinoma, testicular cancer, and stomach cancer.

7. Method of Vaccination

Provided herein is a method for treating or preventing cancer which comprises administering the inventive vaccine, preferably as part of a pharmaceutically acceptable composition, to a mammal in need thereof. The method of administering the vaccine, or vaccination, can be provided to induce a therapeutic and/or prophylactic immune response. The vaccination process can generate in the mammal an immune response against one or more of the cancer antigens as disclosed herein. The vaccine can be administered to an individual to modulate the activity of the mammal's immune system and enhance the immune response. The administration of the vaccine can be the transfection of the one or more cancer antigens as disclosed herein as a nucleic acid molecule that is expressed in the cell and thus, delivered to the surface of the cell upon which the immune system recognizes and induces a cellular, humoral, or cellular and humoral response. The administration of the vaccine can be used to induce or elicit an immune response in mammals against one or more of the cancer antigens by administering to the mammals the vaccine as discussed herein.

Upon administration of the vaccine to the mammal, and thereupon the vector into the cells of the mammal, the transfected cells will express and secrete one or more of the cancer antigens as disclosed herein. These secreted proteins, or synthetic antigens, will be recognized as foreign by the immune system, which will mount an immune response that can include: antibodies made against the one or more cancer antigens, and/or a T-cell response specifically against the one or more cancer antigens. In some examples, a mammal vaccinated with the vaccines discussed herein will have a primed immune system and when challenged with the one or more cancer antigens as disclosed herein, the primed immune system will allow for rapid clearing of subsequent cancer antigens as disclosed herein, whether through the humoral, cellular, or both cellular and humoral immune responses. The vaccine can be administered to an individual to modulate the activity of the individual's immune system, thereby enhancing the immune response.

Methods of administering a DNA vaccine are described in, for example, U.S. Pat. Nos. 4,945,050 and 5,036,006.

The vaccine can be administered to a mammal to elicit an immune response in a mammal. The mammal can be a canine (dog), human, a non-human primate, a cow, a pig, a sheep, a goat, an antelope, a bison, a water buffalo, a bovid, a deer, a hedgehog, an elephant, a llama, an alpaca, a mouse, a rat, or a chicken. Preferably, the mammal is a canine, human, cow, pig, or chicken.

The vaccine dose can be between 1 μg to 10 mg active component/kg body weight/time and can be 20 μg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, 10, or more doses.

a. Method of Generating an Immune Response with the Vaccine

The vaccine can be used to generate an immune response in a mammal, including therapeutic or prophylactic immune response. The immune response can generate antibodies and/or killer T cells which are directed to the one or more cancer antigens as disclosed herein. Such antibodies and T cells can be isolated. In one embodiment, the invention provides a method of inducing an immune response against a telomerase reverse transcriptase (TERT) (e.g., hTERT or dTERT) in a mammal, which method comprises administering the vaccine described herein to a mammal in need thereof, whereby the nucleic acid molecule is expressed in the mammal and one or more of the following immune responses are induced: (a) a humoral immune response specific to a TERT, (b) an inflammatory response comprising increased levels of tumor necrosis factor-α (TNF-α) and interferon-γ (IFN-γ) as compared to a mammal not administered the vaccine, and (c) a cellular immune response specific to a TERT.

Some embodiments provide methods of generating immune responses against one or more of the cancer antigens as disclosed herein, which comprise administering the vaccine to a mammal in need thereof. Some embodiments provide methods of prophylactically vaccinating a mammal against a cancer or tumor expressing one or more of the cancer antigens as described above, which comprise administering the vaccine to a mammal in need thereof. Some embodiments provide methods of therapeutically vaccinating a mammal that has been suffering from the cancer or tumor expressing one or more of the cancer antigens, which comprise administering the vaccine to a mammal in need thereof. Diagnosis of the cancer or tumor expressing the one or more cancer antigens as disclosed herein prior to administration of the vaccine can be performed using routine diagnostic methods.

b. Method of Cancer Treatment with the Vaccine

The vaccine can be used to generate or elicit an immune response in a mammal that is reactive or directed to a cancer or tumor (e.g., melanoma, head and neck, cervical, liver, prostate, blood cancers, esophageal squamous, gastric, etc.) in the mammal or subject in need thereof. The elicited immune response can prevent cancer or tumor growth.

The elicited immune response can prevent and/or reduce metastasis of cancerous or tumor cells. Accordingly, the vaccine can be used in a method that treats and/or prevents cancer or tumors in the mammal or subject administered the vaccine. Depending upon the antigen used in the vaccine, the treated cancer or tumor can be any type of cancer known in the art and described herein, such as, but not limited to, melanoma, blood cancers (e.g., leukemia, lymphoma, myeloma), lung carcinomas (e.g., non-small cell lung carcinoma), esophageal squamous cell carcinomas, bladder cancer, colorectal cancer, esophagus, gastric cancer, hepatocarcinoma, head and neck cancer, brain cancer (e.g., glioblastoma), anal cancer, pancreatic cancer, synovial carcinoma, prostate cancer, testicular cancer, liver cancer, cervical cancer, recurrent respiratory papillomatosis (RRP), skin cancer and stomach cancer.

In some embodiments, the administered vaccine can mediate clearance or prevent growth of tumor cells by (1) inducing humoral immunity via B cell responses to generate antibodies that block monocyte chemoattractant protein-1 (MCP-1) production, thereby retarding myeloid derived suppressor cells (MDSCs) and suppressing tumor growth; (2) increasing cytotoxic T lymphocytes such as $CD8^+$ (CTL) to attack and kill tumor cells; (3) increasing T helper cell responses; (4) increasing inflammatory responses via IFN-γ and TFN-α as compared to an untreated mammal, or preferably all of the aforementioned responses.

In some embodiments, the immune response can generate a humoral immune response and/or an antigen-specific cytotoxic T lymphocyte (CTL) response that does not cause damage to or inflammation of various tissues or systems (e.g., brain or neurological system, etc.) in the subject administered the vaccine.

In some embodiments, the administered vaccine can increase tumor-free survival, reduce tumor mass, increase tumor survival, or a combination thereof in the subject. The administered vaccine can increase tumor free survival by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% in the subject. The administered vaccine can reduce tumor mass by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, and 70% in the subject after immunization. The administered vaccine can prevent and block increases in monocyte chemoattractant protein 1 (MCP-1), a cytokine secreted by myeloid derived suppressor cells, in the subject. In some embodiments, the administered vaccine can prevent and block increases in MCP-1 within the cancerous or tumor tissue in the subject, thereby reducing vascularization of the cancerous or tumor tissue in the subject.

The administered vaccine can increase tumor survival by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, and 70% in the subject. In some embodiments, the vaccine can be administered to the periphery (as described in more detail below) to establish an antigen-specific immune response targeting the cancerous or tumor cells or tissue to clear or eliminate the cancer or tumor expressing the one or more cancer antigens without damaging or causing illness or death in the subject administered the vaccine.

The administered vaccine can increase a cellular immune response in the subject by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold. In some embodiments, the administered vaccine can increase the cellular immune response in the subject by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold.

The administered vaccine can increase interferon gamma (IFN-γ) levels in the subject by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to a subject that has not been treated with the inventive vaccine. In some embodiments, the administered vaccine can increase IFN-γ levels in the subject by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to a subject that has not been treated with the inventive vaccine.

The vaccine dose can be between 1 μg to 10 mg active component/kg body weight/time and can be 20 μg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, or 10.

8. Routes of Administration

The vaccine or pharmaceutical composition can be administered by different routes including, for example, oral, parenteral, sublingual, transdermal, rectal, transmucosal, topical, inhalation, buccal administration, intrapleural, intravenous, intraarterial, intraperitoneal, subcutaneous, intramuscular, intranasal, intrathecal, intraarticular, or combinations thereof. For veterinary use, the composition can be administered as a suitably acceptable formulation in accordance with normal veterinary practice. The veterinarian can readily determine the dosing regimen and route of administration that is most appropriate for a particular animal. The vaccine can be administered by traditional syringes, needleless injection devices, "microprojectile bombardment gone guns," or other physical methods such as electroporation ("EP"), "hydrodynamic method," or ultrasound.

The vaccine can be administered to the mammal by several well-known technologies including DNA injection (also referred to as DNA vaccination) with and without in vivo electroporation, liposome mediated, nanoparticle facilitated, recombinant vectors such as recombinant adenovirus, recombinant AAV and recombinant vaccinia virus. The one or more cancer antigens of the vaccine can be administered via DNA injection and/or in vivo electroporation.

a. Electroporation

The vaccine or pharmaceutical composition can be administered by electroporation. Administration of the vaccine via electroporation can be accomplished using electroporation devices that can be configured to deliver to a desired tissue of a mammal a pulse of energy effective to cause reversible pores to form in cell membranes, and preferable the pulse of energy is a constant current similar to a preset current input by a user. The electroporation device can comprise an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation can be accomplished using an in vivo electroporation device, for example CELLECTRA® EP system (Inovio Pharmaceuticals, Inc., Plymouth Meeting, Pa.) or Elgen electroporator (Inovio Pharmaceuticals, Inc.) to facilitate transfection of cells by the plasmid.

Examples of electroporation devices and electroporation methods that can facilitate administration of the DNA vaccines of the present invention include those described in, for example, U.S. Pat. No. 7,245,963 and U.S. Patent Publication No. 2005/0052630. Other electroporation devices and electroporation methods that can be used for facilitating administration of the DNA vaccines include those described in, for example, U.S. Patent Application Publication No. 2008/0091135.

U.S. Pat. No. 7,245,963 describes modular electrode systems and their use for facilitating the introduction of a biomolecule into cells of a selected tissue in a body or plant. The modular electrode systems can comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then administering via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes.

U.S. Patent Application Publication No. 2005/0052630 describes an electroporation device which can be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk.

The electrode arrays and methods described in U.S. Pat. No. 7,245,963 and U.S. Patent Application Publication No. 2005/0052630 can be adapted for deep penetration into not only tissues such as muscle, but also other tissues or organs. Because of the configuration of the electrode array, the injection needle is also inserted completely into the target organ, and the injection is administered perpendicular to the target issue, in the area that is pre-delineated by the electrodes. The electrodes described in U.S. Pat. No. 7,245,963 and U.S. Patent Application Publication No. 2005/005263 are preferably 20 mm long and 21 gauge.

Additionally, in some embodiments the electroporation device can be a device that is described in, for example, U.S. Pat. Nos. 5,273,525; 6,110,161; 6,261,281; 6,958,060; and 6,939,862. Furthermore, methods described in U.S. Pat. No. 6,697,669, which concerns administration of DNA using any of a variety of devices, and U.S. Pat. No. 7,328,064, which relates to a method of injecting DNA also can be used in the context of the invention.

9. Method of Preparing the Vaccine

Provided herein are methods for preparing the DNA plasmids that comprise the vaccines discussed herein. The DNA plasmids, after the final subcloning step into the mammalian expression plasmid, can be used to inoculate a cell culture in a large scale fermentation tank, using methods known in the art.

The DNA plasmids for use with the EP devices of the present invention can be formulated or manufactured using a combination of known devices and techniques, but preferably they are manufactured using an optimized plasmid manufacturing technique that is described in, for example, U.S. Patent Application Publication 2009/0004716. In some embodiments, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Patent Application Publication No. 2009/0004716 and U.S. Pat. No. 7,238,522.

The present invention has multiple aspects, illustrated by the following non-limiting examples.

10. EXAMPLES

Example 1

This example describes a method of generating a plasmid vaccine comprising a polynucleotide sequence encoding a dTERT antigen.

pGX1414 is a DNA plasmid comprising the polynucleotide sequence of SEQ ID NO: 3, which comprises a polynucleotide sequence of SEQ ID NO: 1 that encodes synthetic consensus dog telomerase reverse transcriptase (SYNCON dTERT), operably linked to a human CMV promoter (hCMV promoter) and a bovine growth hormone poly-adenylation signal (bGH polyA). The plasmid backbone includes the kanamycin resistance gene ($Kan^R$) and plasmid origin of replication (pUC ori). The genetic elements of pGX1414 are set forth in Table 1, and a schematic diagram of pGX1414 is depicted in FIG. 1.

TABLE 1

| Elements | Base Pairs |
|---|---|
| hCMV Promoter | 137-724 |
| SynCon dTERT Coding Sequence | 742-4164 |
| bGH Poly A | 4215-4439 |
| Kanamycin Resistance Gene ($Kan^R$) | 4612-5406 |
| pUC Ori | 5705-6378 |

pGX1414 was generated by cloning the synthetic consensus dog telomerase reverse transcriptase (SYNCON dTERT) into pGX0001 at the BamHI and NotI sites. To generate the consensus dog TERT sequence, 19 TERT sequences were collected from GenBank, and the consensus sequence was obtained after performing sequence alignment using Clustal W (DNASTAR). At the positions that contain residues with great diversity (defined as 'Disagreement Level 1 and 2' by the software), selection of amino acids was weighted towards the native dog TERT.

The GenBank accession numbers used to generate the consensus dog TERT sequence are as follows: NP_001026800, NP_001026800.1, XP_004411686, XP_004768446, XP_004812556, EFB14781, XP_004812554, XP_004768447, XP_004440093, XP_004411687, XP_004812555, XP_004274558, NP_937983, AAC51724, NP_001177896, XP_004380340, NP_001039707, XP_003950543, NP_001231229, and DAA17756.

Once the consensus dTERT sequence was obtained, two mutations (R579Y and D996Y) were incorporated to assist in breaking tolerance (see, e.g., Gross et al., *J. Clin. Invest.,* 113: 425-433 (2004)). Additionally, five mutations (K633A, R638A, D719A, Y724A and D876A) were introduced to abolish telomerase activity (see, e.g., Weinrich et al., *Nature Genetics,* 17: 498-502 (1997)). The final modified consensus dTERT sequence shares 95.4% sequence identity with the native dog TERT amino acid sequence. An upstream Kozak sequence and an IgE leader sequence were added to the N-terminal to increase expression. In order to maximize expression levels, the codon usage of the consensus dTERT sequence was adapted to the codon bias of mammalian genes. DNA optimization for RNA translation also was performed: regions of very high (>80%) or very low (<30%) GC content and the cis-acting sequence motifs such as internal TATA boxes, chi-sites and ribosomal entry sites were avoided. The synthesized SYNCON dTERT was digested with BamHI and NotI, and cloned into the expression vector pGX0001.

The consensus dTERT coding sequence (SEQ ID NO: 1) was cloned into pGX0001 (a modified pVAX1 expression vector) between the human cytomegalovirus immediate-early promoter (hCMV promoter) and the bGH polyA. The original pVAX1 expression vector was obtained from Life Technologies (Carlsbad, Calif.). A map of the modified pVAX1 (pGX0001) expression vector is shown in FIG. 2.

The modifications introduced into pVAX1 to create pGX0001 were based on the reported sequence of pVAX1 available from Life Technologies. These modifications are set forth below and do not impede plasmid amplification or antigen transcription and translation. No further changes in the sequence of pGX0001 have been observed to date in any of the plasmid products using pGX0001 as the backbone.

C>G 241 in CMV promoter

C>T 1158 backbone, downstream of the bovine growth hormone polyadenylation signal (bGH polyA)

A>-2092 backbone, downstream of the Kanamycin resistance gene (KanR)

C>T 2493 in pUC origin of replication (pUC ori)

G>C 2969 in very end of pUC Ori upstream of RNASeH site, and base pairs 2, 3 and 4 were changed from ACT to CTG in backbone, upstream of CMV promoter.

The results of this example demonstrate the generation of the inventive vaccine.

Example 2

This example demonstrates the immunogenicity of the inventive dTERT-expressing vaccine in mice.

The ability of pGX1414 (described in Example 1) to induce cell-mediated immune responses in C57BL/6 mice was examined. Briefly, female 8-week-old C57BL/6 mice (n=5) were divided into two groups: a naïve group and a group immunized with 25 μg of pGX1414 by intramuscular injection (IM) into the quadriceps followed by electroporation (EP) using the CELLECTRA® adaptive constant current device (Inovio Pharmaceuticals Inc., Plymouth Meeting, Pa.). The device was configured to deliver two 0.1 Amp pulses of 52 ms pulse width spaced apart by a one second delay. Mice received four immunizations two weeks apart. One week after the last immunization, mice were sacrificed, spleens recovered, the splenocytes were isolated, and a mouse IFN-γ ELISpot assay was performed to evaluate antigen-specific cellular responses as previously described (Yan et al., Cancer Immunology Research (2013)) (see FIG. 3A). Briefly, ELISpot 96-well plates were coated with the monoclonal antibody to mouse IFN-γ (R&D Systems, Minneapolis, Minn.) diluted in PBS, and incubated overnight at 4° C. The next day, plates were washed and blocked for two hours at room temperature with PBS supplemented with 1% BSA and 5% sucrose. Mice splenocytes from both study groups were independently added in triplicate at an input cell number of $2\times10^5$ cells per well resuspended in complete culture medium (RPMI 1640 supplemented with 10% FBS). Two sets of peptides, synthesized by GenScript (Piscataway, N.J.) and each containing 15 amino acids overlapping by nine amino acids, representing either the entire native dog TERT (dTERT) protein or the SYNCON dTERT protein described in Example 1, were pooled at a concentration of 2 μg/ml peptide into four pools. Concavalin A at 5 μg/ml was used as a positive control and complete culture medium was used as a negative control, respectively. Splenocytes and peptides containing plates were incubated for 24 hours at 37° C., in a 5% $CO_2$ atmosphere incubator. The plates were then washed and a biotinylated anti-mouse IFN-γ detection antibody was added, and plates were incubated overnight at 4° C. The plates were washed, and color development was followed according to the manufacturer's instructions (ELISpot Blue Color Module, R&D Systems, Minneapolis, Minn.). The spots on the plates were counted using an automated ELISPOT reader (Cellular Technology, Shaker Heights, Ohio). The average number of Spot Forming Units (SFU) was adjusted to $1\times10^6$ splenocytes for data display.

As shown in FIG. 3B, the total response against four pools of SYNCON dTERT peptides in pGX1414-immunized mice was $448\pm10^3$ SFU/$10^6$ splenocytes, which was significantly greater than the background responses in the naïve group (17±8 SFU/$10^6$ splenocytes) ($p<0.05$). In addition, the immune responses induced by pGX1414 against the native dTERT peptides were evaluated. The additive response against four pools of native dTERT peptides in pGX1414-immunized mice was 266±98 SFU/$10^6$ splenocytes, while the background responses in the naïve group were 14±4 SFU/$10^6$ splenocytes ($p<0.05$), as shown in FIG. 3C.

The results of this example demonstrate that the inventive dTERT-encoding vaccine was able to generate immune responses against both matched SYNCON dTERT as well as native dTERT peptides in mice.

The results of this example demonstrate the generation of the inventive vaccine.

Figure 5:
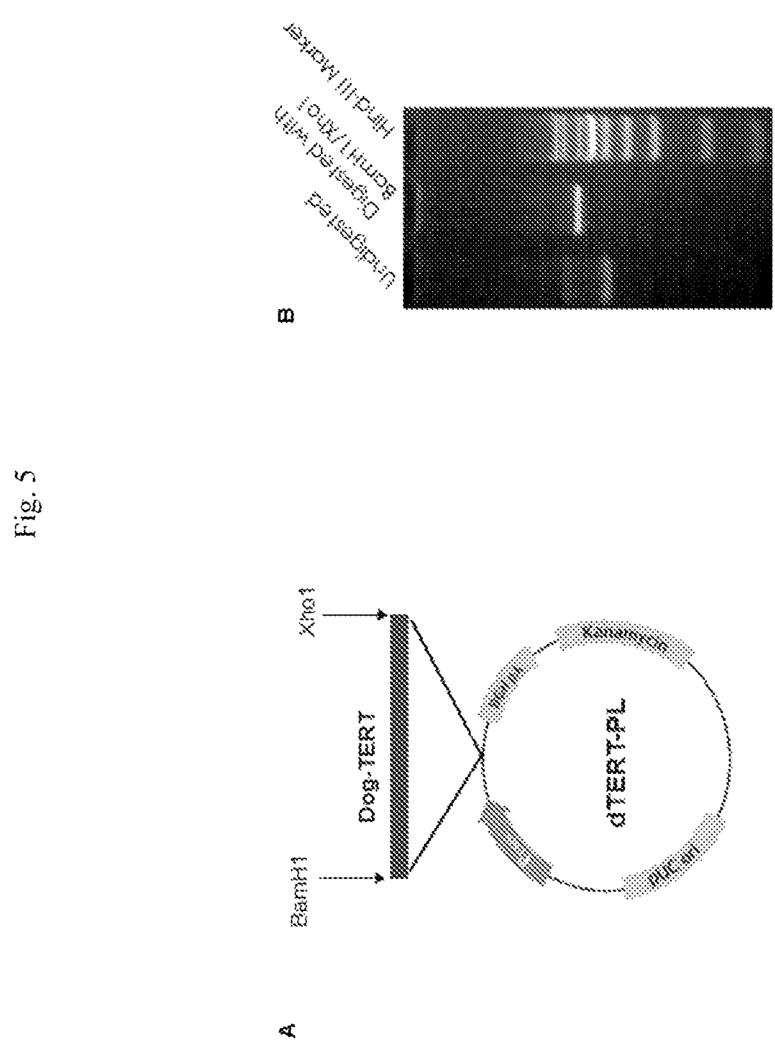

Example 3 pGX1415 is a DNA plasmid comprising the polynucleotide sequence of SEQ ID NO: 4, which encodes SEQ ID NO:5. SEQ ID NO:5 is a dog telomerase reverse transcriptase (dTERT) polypeptide having seven point mutations that abolish telomerase activity (resulting in substitutions: R579Y, D996Y, K633A, R638A, D719A, Y724A and D876A), operably linked to a human CMV promoter (hCMV promoter) and a bovine growth hormone polyadenylation signal (bGH polyA). The plasmid backbone includes the kanamycin resistance gene ($Kan^R$) and plasmid origin of replication (pUC ori). The genetic elements of pGX1415 are set forth in Table 2, and a schematic diagram of pGX1415 is depicted in FIG. 5.

TABLE 2

| Elements | Base Pairs |
|---|---|
| hCMV Promoter | 137-724 |
| dTERT-PL Coding Sequence | 742-4164 |

TABLE 2-continued

| Elements | Base Pairs |
|---|---|
| bGH Poly A | 4208-4432 |
| Kanamycin Resistance Gene ($Kan^R$) | 4605-5399 |
| pUC Ori | 5698-6371 |

pGX1415 was generated by cloning SEQ ID NO:4 into pGX0001 at the BamHI and XhoI sites.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the present disclosure are set out in the following numbered clauses:

Clause 1. A vaccine comprising a nucleic acid molecule comprising a polynucleotide sequence selected from the group consisting of the polynucleotide sequence of SEQ ID NO: 1, a polynucleotide sequence that is at least 95% identical to SEQ ID NO: 1; a polynucleotide sequence encoding the amino acid sequence of SEQ ID NO: 2; and a polynucleotide sequence encoding an amino acid sequence that is at least 95% identical to SEQ ID NO:2; or any combination thereof.

Clause 2. The vaccine of clause 1, wherein the nucleic acid molecule comprises the polynucleotide sequence of SEQ ID NO: 1.

Clause 3. The vaccine of clause 1, wherein the nucleic acid molecule comprises a polynucleotide sequence that is 95% identical to SEQ ID NO: 1.

Clause 4. The vaccine of clause 1, wherein the nucleic acid molecule comprises a polynucleotide sequence encoding the amino acid sequence of SEQ ID NO: 2.

Clause 5. The vaccine of clause 1, wherein the nucleic acid molecule comprises a polynucleotide sequence encoding an amino acid sequence that is 95% identical to SEQ ID NO: 2.

Clause 6. The vaccine of any one of clauses 1-5, wherein the nucleic acid molecule is a plasmid.

Clause 7. The vaccine of clause 6, wherein the plasmid comprises the nucleic acid sequence of SEQ ID NO:3.

Clause 8. The vaccine of any one of clauses 1-7, further comprising an adjuvant.

Clause 9. The vaccine of clause 8, wherein the adjuvant is IL-12, IL-15, IL-28, or RANTES.

Clause 10. A method of inducing an immune response against a telomerase reverse transcriptase (TERT) in a mammal, which method comprises administering the vaccine of any one of claims 1-9 to a mammal in need thereof, whereby the nucleic acid molecule is expressed in the mammal and one or more of the following immune responses are induced:

(a) a humoral immune response specific to a TERT, (b) an inflammatory response comprising increased levels of tumor necrosis factor-$\alpha$ (TNF-$\alpha$) and interferon-$\gamma$ (IFN-$\gamma$) as compared to a mammal not administered the vaccine, and (c) a cellular immune response specific to a TERT.

Clause 11. The method of clause 10, wherein the TERT is dog TERT (dTERT).

Clause 12. The method of any one of clauses 10-11, wherein the mammal has cancer.

Clause 13. A method of treating a cancer in a mammal, which method comprises administering to a mammal in need thereof a composition comprising the vaccine of any one of claims 1-9 and a pharmaceutically acceptable carrier, whereby the nucleic acid molecule is expressed in the mammal and the cancer is treated.

Clause 14. The method of any one of clauses 10-13, wherein the vaccine is administered via electroporation.

Clause 15. The method of any one of clauses 10-14, wherein the mammal is a dog.

Clause 16. The method of any one of clauses 13-15, wherein the cancer is selected from the group consisting of melanoma, prostate cancer, liver cancer, cervical cancer, recurrent respiratory papillomatosis (RRP), anal cancer, head and neck cancer, blood cancers, leukemia, lymphoma, myeloma, lung carcinomas, non-small cell lung carcinoma, esophageal squamous cell carcinomas, bladder cancer, colorectal cancer, gastric cancer, hepatocarcinoma, brain cancer, glioblastoma, pancreatic cancer, synovial carcinoma, testicular cancer, and stomach cancer.

Clause 17. A nucleic acid molecule comprising the polynucleotide sequence of SEQ ID NO:1 or a polynucleotide sequence that is at least 95% identical to SEQ ID NO: 1.

Clause 18. A nucleic acid molecule comprising a polynucleotide encoding the amino acid sequence of SEQ ID NO: 2.

Clause 19. The nucleic acid molecule of clause 17 or clause 18, which comprises a polynucleotide sequence of SEQ ID NO: 3.

Clause 20. A polypeptide comprising the amino acid sequence of SEQ ID NO: 2, the amino acid sequence of SEQ ID NO:5, an amino acid sequence that is at least 95% identical to SEQ ID NO: 2.

What is claimed is:

1. A vaccine comprising a nucleic acid molecule comprising a polynucleotide sequence encoding a dog telomerase reverse transcriptase (dTERT) antigen, wherein the polynucleotide sequence is selected from the group consisting of:

the polynucleotide sequence of SEQ ID NO: 1;

a polynucleotide sequence that is at least 95% identical to SEQ ID NO: 1, wherein the dTERT antigen encoded by the polynucleotide sequence comprises the following amino acid substitutions relative to a wild-type dTERT antigen: R579Y, D996Y, K633A, R638A, D719A, Y724A and D876A;

a polynucleotide sequence encoding the amino acid sequence of SEQ ID NO: 2;

a polynucleotide sequence encoding an amino acid sequence that is at least 95% identical to SEQ ID NO:2, wherein the dTERT antigen comprises the following amino acid substitutions relative to a wild-type dTERT antigen: R579Y, D996Y, K633A, R638A, D719A, Y724A and D876A; and any combination thereof.

2. The vaccine of claim 1, wherein the nucleic acid molecule comprises the polynucleotide sequence of SEQ ID NO: 1.

3. The vaccine of claim 1, wherein the nucleic acid molecule comprises a polynucleotide sequence that is at least 95% identical to SEQ ID NO: 1, wherein the dTERT antigen encoded by the polynucleotide sequence comprises the following amino acid substitutions relative to a wild-type dTERT antigen: R579Y, D996Y, K633A, R638A, D719A, Y724A and D876A.

4. The vaccine of claim 1, wherein the nucleic acid molecule comprises a polynucleotide sequence encoding the amino acid sequence of SEQ ID NO: 2.

5. The vaccine of claim 1, wherein the nucleic acid molecule comprises a polynucleotide sequence encoding an amino acid sequence that is at least 95% identical to SEQ ID NO: 2, wherein the dTERT antigen comprises the following amino acid substitutions relative to a wild-type dTERT antigen: R579Y, D996Y, K633A, R638A, D719A, Y724A and D876A.

6. The vaccine of claim 1, wherein the nucleic acid molecule is a plasmid.

7. The vaccine of claim 6, wherein the plasmid comprises the nucleic acid sequence of SEQ ID NO:3.

8. The vaccine of claim 7, further comprising an adjuvant.

9. The vaccine of claim 8, wherein the adjuvant is IL-12, IL-15, IL-28, or RANTES.

10. A method of inducing an immune response against a dog telomerase reverse transcriptase (dTERT) antigen in a mammal, which method comprises administering the vaccine of claim 1 to the mammal, whereby the nucleic acid molecule is expressed in the mammal and one or more of the following immune responses are induced:

(a) a humoral immune response specific to a TERT, (b) an inflammatory response comprising an increased level of interferon-γ (IFN-γ) as compared to a mammal not administered the vaccine, and (c) a cellular immune response specific to a TERT.

11. The method of claim 10, wherein the mammal has cancer.

12. The method of claim 11, wherein the cancer is selected from the group consisting of melanoma, prostate cancer, liver cancer, cervical cancer, recurrent respiratory papillomatosis (RRP), anal cancer, head and neck cancer, blood cancers, leukemia, lymphoma, myeloma, lung carcinomas, non-small cell lung carcinoma, esophageal squamous cell carcinomas, bladder cancer, colorectal cancer, gastric cancer, hepatocarcinoma, brain cancer, glioblastoma, pancreatic cancer, synovial carcinoma, testicular cancer, and stomach cancer, or any combination thereof.

13. A nucleic acid molecule comprising:

the polynucleotide sequence of SEQ ID NO:1; or a polynucleotide sequence encoding a dog telomerase reverse transcriptase (dTERT) antigen that is at least 95% identical to SEQ ID NO: 1, wherein the dTERT antigen encoded by the polynucleotide sequence comprises the following amino acid substitutions relative to a wild-type dTERT antigen: R579Y, D996Y, K633A, R638A, D719A, Y724A and D876A.

14. A nucleic acid molecule comprising:

a polynucleotide sequence encoding the amino acid sequence of SEQ ID NO: 2; or an amino acid sequence of a dog telomerase reverse transcriptase (dTERT) antigen that is at least 95% identical to SEQ ID NO:2, wherein the dTERT antigen comprises the following amino acid substitutions relative to a wild-type dTERT antigen: R579Y, D996Y, K633A, R638A, D719A, Y724A and D876A.

15. The nucleic acid molecule of claim 13, which comprises a polynucleotide sequence of SEQ ID NO: 3.

16. A polypeptide comprising:

the amino acid sequence of SEQ ID NO: 2; or an amino acid sequence of a dog telomerase reverse transcriptase (dTERT) antigen that is at least 95% identical to SEQ ID NO: 2, wherein the dTERT antigen comprises the following amino acid substitutions relative to a wild-type dTERT antigen: R579Y, D996Y, K633A, R638A, D719A, Y724A and D876A.

* * * * *

SEQUENCE LISTING

```
<160> NUMBER OF SEQ ID NOS: 7

<210> SEQ ID NO 1
<211> LENGTH: 3423
<212> TYPE: DNA
<213> ORGANISM: Artificial Sequence
<220> FEATURE:
<223> OTHER INFORMATION: dTERT pGX1414 insert

<400> SEQUENCE: 1

atggactgga cctggattct gttcctggtg gctgctgcta ctcgggtgca ttccccaaga     60
```

```
gccccaagat gtcgcgctgt gagagctctg ctgcggggaa gatacaggga ggtgctgcca    120
ctggccacct tcctgcggag actgggccct caggggaggc gcctggtgcg acgaggcgac    180
ccagcagctt ttcgggcact ggtggcacag tgcctggtgt gcgtgccatg ggatgccaga    240
ccccctccag cagcaccaag ctttaggcag gtctcctgcc tgaaggagct ggtggcacga    300
gtggtccagc ggctgtgcga aaggggagct cgaaacgtgc tggccttcgg gtttgctctg    360
ctggacggag cacgaggagg accacctgtc gccttcacca catccgtgcg gtcttacctg    420
cccaatacag tgactgagac cctgagaggc agcggagcat ggggactgct gctgagaagg    480
gtcggggacg atgtgctgac ccacctgctg gctagatgcg cactgtatct gctggtcgca    540
ccatcatgcg cataccaggt gtgcggacca ccactgtatg acctgtgcgc tcccgcaagc    600
ctgcccctgc ctgccccagg actgccagga ctgcctggac tgccaggact gggacatggc    660
gctgggactt ccgcagatct gcgacctacc cgacaggcac agaactctgg agctcgccga    720
cggagaggaa gtccaggcag ctccgtccca ctggcaaaaa ggcctaggcg ctctgtggct    780
ccagagcctg aaaggggagc acaccgcagt ttccctcgag cacatcagcc tccagtctca    840
gagccacctg cagtgactcc agctagggct gcagccgagg ctgcaagctg ggaaggagga    900
ccaccaggaa ctcgaccatc cacccctgca tggcacccat acccaggacc tcagggagtg    960
ccacacgatc ccgctcatcc tgagaccaag catttcctgt attgctccgg gggacgcgaa   1020
cgactgcgac catcttttct gctgagtgcc ctgcctccat ctctgaccgg ggctaggaaa   1080
ctggtggaga caatctttct gggaagtgcc ccacagaagc caggagcagc tcgacgaatg   1140
agaaggctgc ctgctcgcta ctggagaatg aggccactgt tccaggaact gctggggaac   1200
cacgcacggt gcccttatag agccctgctg aggacccatt gtccactgag ggccatggca   1260
gccaaggagg caagcggaaa tcaggcccac cgcggagtcg gcatttgccc tctggaacga   1320
ccagtggctg caccagagga acagaccgac ccccgccgac tggtgcagct gctgcgccag   1380
cattctagtc cttggcaggt gtacgcattc ctgcgagcat gcctgtgccg actggtgcca   1440
acaggactgt gggggtcccg acacaaccag cggagattcc tgcggaacgt gaagaagttc   1500
atctcactgg gcaagcatgc caaactgagc ctgcaggagc tgacatggaa gatgaaagtg   1560
caggattgtg catggctgag gggaagccca ggagcatgct gcgtgccagc agctgaacac   1620
aggcgccgag aggaaattct ggcccggttc ctggtgtggc tgatgggaca tatctacgtg   1680
gtcgagctgc tgagaagctt cttttatgtg accgaaacta cctttcagaa gaactacctg   1740
ttcttttatc gcaaaagcgt gtggtcacag ctgcagtcca tcggcattag acagcacttc   1800
aatagtgtcc atctgaggga gctgtcagag gccgaagtgc ggagacacag agaagccagg   1860
cctgctctgc tgacatcccg cctgcgattc ctgccagctc cctctggcct ggcaccaatt   1920
gtcaacatgg actacgtgat gggggcccgc actttccacc gagataagaa agtgcagcat   1980
ctgaccagcc aggtcaaaac actgttttcc gtgctgaatt atgagcgagc taggcgcccc   2040
tctctgctgg gagcaagtgt gctgggaatg gacgatatcc accgagcatg gcgaaccttc   2100
gtcctgcggg tgagagctca ggaccctgca ccacagctgt actttgtgaa ggtcgctgtg   2160
acaggagcag cagacgcact gccacaggat agactggtcg aagtgatcgc caacgtcatt   2220
cgcccccagg aaaatactta ctgcgtgcgg cactatgctg tggtccgacg aaccgcacga   2280
ggacacgtca gaaagtcctt caaacggcac gtgagcacct tcaccgacct gcagccctat   2340
atgcgccagt ttgtggagcg gctgcaggaa acatcaagcc tgagagatgc cgtggtcatt   2400
gagcagtcct ctagtctgaa cgaagctggg tccggactgt tccacctgtt tctgagactg   2460
```

```
gtccacaatc atgtgatcag gattggcggg aaaagttaca tccagtgtca gggcattcct   2520

caggggagca tcctgtccac cctgctgtgc tcactgtgct atggcgacat ggagagaagg   2580

ctgttcccag gcatccagca ggacggggtc ctgctgcgac tggtggccga tttcctgctg   2640

gtgacacctc acctgactca ggcccaggct tttctgagga cactggtccg cggcgtgcca   2700

gagtacggat gcagagccaa cctgcagaag actgctgtca atttccctgt ggaagatggg   2760

gccctgggat ctgctgcacc tctgcagctg ccagctcatt gcctgtttcc atggtgtggc   2820

ctgctgctgg acaccaggac actggaagtg agctgtgatt actcaagcta tgcacgaaca   2880

tcaattcggg ccagcctgac tttttcccag ggagccaagc ccggcagaaa catgcgccga   2940

aaactgttcg ccgtgctgag gctgaagtgc tgtgctctgt ttctgtacct gcaggtgaac   3000

agcattcaca cagtctacat gaacgtgtac aaaatcttcc tgctgcaggc ctatcggttt   3060

catgcttgcg tcctgcagct gcccttcaac cagcctgtgc gcaagaatcc tagtttcttt   3120

ctgagagtga tctctgatac tgccagttgc tgttactcac tgctgaaagc aaggaatgcc   3180

ggcatgtctc tgggcgctaa gggggcatca ggactgttcc caagcgaggc agctcgatgg   3240

ctgtgcctgc acgcttttct gctgaaactg gcaagacatt ccgggactta taggtgtctg   3300

ctgggagccc tgagagcagc caaggctcac ctgtctagac agctgcccag ggcaccctg    3360

gccgcactgg aagcagcagc agacccaagc ctgaccgcag atttcaaaac tatcctggac   3420

tga                                                                 3423
```

<210> SEQ ID NO 2
<211> LENGTH: 1140
<212> TYPE: PRT
<213> ORGANISM: Artificial Sequence
<220> FEATURE:
<223> OTHER INFORMATION: dTERT pGX1414 insert

<400> SEQUENCE: 2

```
Met Asp Trp Thr Trp Ile Leu Phe Leu Val Ala Ala Ala Thr Arg Val
1               5                   10                  15

His Ser Pro Arg Ala Pro Arg Cys Arg Ala Val Arg Ala Leu Leu Arg
            20                  25                  30

Gly Arg Tyr Arg Glu Val Leu Pro Leu Ala Thr Phe Leu Arg Arg Leu
        35                  40                  45

Gly Pro Gln Gly Arg Arg Leu Val Arg Arg Gly Asp Pro Ala Ala Phe
    50                  55                  60

Arg Ala Leu Val Ala Gln Cys Leu Val Cys Val Pro Trp Asp Ala Arg
65                  70                  75                  80

Pro Pro Pro Ala Ala Pro Ser Phe Arg Gln Val Ser Cys Leu Lys Glu
                85                  90                  95

Leu Val Ala Arg Val Val Gln Arg Leu Cys Glu Arg Gly Ala Arg Asn
            100                 105                 110

Val Leu Ala Phe Gly Phe Ala Leu Leu Asp Gly Ala Arg Gly Gly Pro
        115                 120                 125

Pro Val Ala Phe Thr Thr Ser Val Arg Ser Tyr Leu Pro Asn Thr Val
    130                 135                 140

Thr Glu Thr Leu Arg Gly Ser Gly Ala Trp Gly Leu Leu Leu Arg Arg
145                 150                 155                 160

Val Gly Asp Asp Val Leu Thr His Leu Leu Ala Arg Cys Ala Leu Tyr
                165                 170                 175

Leu Leu Val Ala Pro Ser Cys Ala Tyr Gln Val Cys Gly Pro Pro Leu
```

```
            180                 185                 190

Tyr Asp Leu Cys Ala Pro Ala Ser Leu Pro Leu Pro Ala Pro Gly Leu
        195                 200                 205

Pro Gly Leu Pro Gly Leu Pro Gly Leu Gly His Gly Ala Gly Thr Ser
    210                 215                 220

Ala Asp Leu Arg Pro Thr Arg Gln Ala Gln Asn Ser Gly Ala Arg Arg
225                 230                 235                 240

Arg Arg Gly Ser Pro Gly Ser Ser Val Pro Leu Ala Lys Arg Pro Arg
                245                 250                 255

Arg Ser Val Ala Pro Glu Pro Glu Arg Gly Ala His Arg Ser Phe Pro
            260                 265                 270

Arg Ala His Gln Pro Pro Val Ser Glu Pro Pro Ala Val Thr Pro Ala
        275                 280                 285

Arg Ala Ala Ala Glu Ala Ala Ser Trp Glu Gly Gly Pro Pro Gly Thr
    290                 295                 300

Arg Pro Ser Thr Pro Ala Trp His Pro Tyr Pro Gly Pro Gln Gly Val
305                 310                 315                 320

Pro His Asp Pro Ala His Pro Glu Thr Lys His Phe Leu Tyr Cys Ser
                325                 330                 335

Gly Gly Arg Glu Arg Leu Arg Pro Ser Phe Leu Leu Ser Ala Leu Pro
            340                 345                 350

Pro Ser Leu Thr Gly Ala Arg Lys Leu Val Glu Thr Ile Phe Leu Gly
        355                 360                 365

Ser Ala Pro Gln Lys Pro Gly Ala Ala Arg Arg Met Arg Arg Leu Pro
    370                 375                 380

Ala Arg Tyr Trp Arg Met Arg Pro Leu Phe Gln Glu Leu Leu Gly Asn
385                 390                 395                 400

His Ala Arg Cys Pro Tyr Arg Ala Leu Leu Arg Thr His Cys Pro Leu
                405                 410                 415

Arg Ala Met Ala Ala Lys Glu Ala Ser Gly Asn Gln Ala His Arg Gly
            420                 425                 430

Val Gly Ile Cys Pro Leu Glu Arg Pro Val Ala Ala Pro Glu Glu Gln
        435                 440                 445

Thr Asp Pro Arg Arg Leu Val Gln Leu Leu Arg Gln His Ser Ser Pro
    450                 455                 460

Trp Gln Val Tyr Ala Phe Leu Arg Ala Cys Leu Cys Arg Leu Val Pro
465                 470                 475                 480

Thr Gly Leu Trp Gly Ser Arg His Asn Gln Arg Arg Phe Leu Arg Asn
                485                 490                 495

Val Lys Lys Phe Ile Ser Leu Gly Lys His Ala Lys Leu Ser Leu Gln
            500                 505                 510

Glu Leu Thr Trp Lys Met Lys Val Gln Asp Cys Ala Trp Leu Arg Gly
        515                 520                 525

Ser Pro Gly Ala Cys Cys Val Pro Ala Ala Glu His Arg Arg Arg Glu
    530                 535                 540

Glu Ile Leu Ala Arg Phe Leu Val Trp Leu Met Gly His Ile Tyr Val
545                 550                 555                 560

Val Glu Leu Leu Arg Ser Phe Phe Tyr Val Thr Glu Thr Thr Phe Gln
                565                 570                 575

Lys Asn Tyr Leu Phe Phe Tyr Arg Lys Ser Val Trp Ser Gln Leu Gln
            580                 585                 590

Ser Ile Gly Ile Arg Gln His Phe Asn Ser Val His Leu Arg Glu Leu
        595                 600                 605
```

```
Ser Glu Ala Glu Val Arg Arg His Arg Glu Ala Arg Pro Ala Leu Leu
    610                 615                 620

Thr Ser Arg Leu Arg Phe Leu Pro Ala Pro Ser Gly Leu Ala Pro Ile
625                 630                 635                 640

Val Asn Met Asp Tyr Val Met Gly Ala Arg Thr Phe His Arg Asp Lys
                645                 650                 655

Lys Val Gln His Leu Thr Ser Gln Val Lys Thr Leu Phe Ser Val Leu
            660                 665                 670

Asn Tyr Glu Arg Ala Arg Arg Pro Ser Leu Leu Gly Ala Ser Val Leu
        675                 680                 685

Gly Met Asp Asp Ile His Arg Ala Trp Arg Thr Phe Val Leu Arg Val
    690                 695                 700

Arg Ala Gln Asp Pro Ala Pro Gln Leu Tyr Phe Val Lys Val Ala Val
705                 710                 715                 720

Thr Gly Ala Ala Asp Ala Leu Pro Gln Asp Arg Leu Val Glu Val Ile
                725                 730                 735

Ala Asn Val Ile Arg Pro Gln Glu Asn Thr Tyr Cys Val Arg His Tyr
            740                 745                 750

Ala Val Val Arg Arg Thr Ala Arg Gly His Val Arg Lys Ser Phe Lys
        755                 760                 765

Arg His Val Ser Thr Phe Thr Asp Leu Gln Pro Tyr Met Arg Gln Phe
    770                 775                 780

Val Glu Arg Leu Gln Glu Thr Ser Ser Leu Arg Asp Ala Val Val Ile
785                 790                 795                 800

Glu Gln Ser Ser Ser Leu Asn Glu Ala Gly Ser Gly Leu Phe His Leu
                805                 810                 815

Phe Leu Arg Leu Val His Asn His Val Ile Arg Ile Gly Gly Lys Ser
            820                 825                 830

Tyr Ile Gln Cys Gln Gly Ile Pro Gln Gly Ser Ile Leu Ser Thr Leu
        835                 840                 845

Leu Cys Ser Leu Cys Tyr Gly Asp Met Glu Arg Arg Leu Phe Pro Gly
    850                 855                 860

Ile Gln Gln Asp Gly Val Leu Leu Arg Leu Val Ala Asp Phe Leu Leu
865                 870                 875                 880

Val Thr Pro His Leu Thr Gln Ala Gln Ala Phe Leu Arg Thr Leu Val
                885                 890                 895

Arg Gly Val Pro Glu Tyr Gly Cys Arg Ala Asn Leu Gln Lys Thr Ala
            900                 905                 910

Val Asn Phe Pro Val Glu Asp Gly Ala Leu Gly Ser Ala Ala Pro Leu
        915                 920                 925

Gln Leu Pro Ala His Cys Leu Phe Pro Trp Cys Gly Leu Leu Leu Asp
    930                 935                 940

Thr Arg Thr Leu Glu Val Ser Cys Asp Tyr Ser Ser Tyr Ala Arg Thr
945                 950                 955                 960

Ser Ile Arg Ala Ser Leu Thr Phe Ser Gln Gly Ala Lys Pro Gly Arg
                965                 970                 975

Asn Met Arg Arg Lys Leu Phe Ala Val Leu Arg Leu Lys Cys Cys Ala
            980                 985                 990

Leu Phe Leu Tyr Leu Gln Val Asn  Ser Ile His Thr Val  Tyr Met Asn
        995                 1000                1005

Val Tyr  Lys Ile Phe Leu Leu  Gln Ala Tyr Arg Phe  His Ala Cys
    1010                1015                1020
```

```
Val Leu  Gln Leu Pro Phe Asn  Gln Pro Val Arg Lys  Asn Pro Ser
    1025                 1030                 1035

Phe Phe  Leu Arg Val Ile Ser  Asp Thr Ala Ser Cys  Cys Tyr Ser
    1040                 1045                 1050

Leu Leu  Lys Ala Arg Asn Ala  Gly Met Ser Leu Gly  Ala Lys Gly
    1055                 1060                 1065

Ala Ser  Gly Leu Phe Pro Ser  Glu Ala Ala Arg Trp  Leu Cys Leu
    1070                 1075                 1080

His Ala  Phe Leu Leu Lys Leu  Ala Arg His Ser Gly  Thr Tyr Arg
    1085                 1090                 1095

Cys Leu  Leu Gly Ala Leu Arg  Ala Ala Lys Ala His  Leu Ser Arg
    1100                 1105                 1110

Gln Leu  Pro Arg Gly Thr Leu  Ala Ala Leu Glu Ala  Ala Ala Asp
    1115                 1120                 1125

Pro Ser  Leu Thr Ala Asp Phe  Lys Thr Ile Leu Asp
    1130                 1135                 1140


<210> SEQ ID NO 3
<211> LENGTH: 6384
<212> TYPE: DNA
<213> ORGANISM: Artificial Sequence
<220> FEATURE:
<223> OTHER INFORMATION: pGX1414 dTERT

<400> SEQUENCE: 3

gctgcttcgc gatgtacggg ccagatatac gcgttgacat tgattattga ctagttatta     60

atagtaatca attacggggt cattagttca tagcccatat atggagttcc gcgttacata    120

acttacggta aatggcccgc ctggctgacc gcccaacgac ccccgcccat tgacgtcaat    180

aatgacgtat gttcccatag taacgccaat agggactttc cattgacgtc aatgggtgga    240

gtatttacgg taaactgccc acttggcagt acatcaagtg tatcatatgc caagtacgcc    300

ccctattgac gtcaatgacg gtaaatggcc cgcctggcat tatgcccagt acatgacctt    360

atgggacttt cctacttggc agtacatcta cgtattagtc atcgctatta ccatggtgat    420

gcggttttgg cagtacatca atgggcgtgg atagcggttt gactcacggg gatttccaag    480

tctccacccc attgacgtca atgggagttt gttttggcac caaaatcaac gggactttcc    540

aaaatgtcgt aacaactccg ccccattgac gcaaatgggc ggtaggcgtg tacggtggga    600

ggtctatata agcagagctc tctggctaac tagagaaccc actgcttact ggcttatcga    660

aattaatacg actcactata gggagaccca agctggctag cgtttaaact taagcttggt    720

accgagctcg gatccgccac catggactgg acctggattc tgttcctggt ggctgctgct    780

actcgggtgc attccccaag agccccaaga tgtcgcgctg tgagagctct gctgcgggga    840

agatacaggg aggtgctgcc actggccacc ttcctgcgga gactgggccc tcaggggagg    900

cgcctggtgc gacgaggcga cccagcagct tttcgggcac tggtggcaca gtgcctggtg    960

tgcgtgccat gggatgccag accccctcca gcagcaccaa gctttaggca ggtctcctgc   1020

ctgaaggagc tggtggcacg agtggtccag cggctgtgcg aaaggggagc tcgaaacgtg   1080

ctggccttcg ggtttgctct gctggacgga gcacgaggag gaccacctgt cgccttcacc   1140

acatccgtgc ggtcttacct gcccaataca gtgactgaga ccctgagagg cagcggagca   1200

tggggactgc tgctgagaag ggtcggggac gatgtgctga cccacctgct ggctagatgc   1260

gcactgtatc tgctggtcgc accatcatgc gcataccagg tgtgcggacc accactgtat   1320

gacctgtgcg ctcccgcaag cctgcccctg cctgccccag gactgccagg actgcctgga   1380
```

```
ctgccaggac tgggacatgg cgctgggact tccgcagatc tgcgacctac ccgacaggca   1440
cagaactctg gagctcgccg acggagagga agtccaggca gctccgtccc actggcaaaa   1500
aggcctaggc gctctgtggc tccagagcct gaaaggggag cacaccgcag tttccctcga   1560
gcacatcagc ctccagtctc agagccacct gcagtgactc cagctagggc tgcagccgag   1620
gctgcaagct gggaaggagg accaccagga actcgaccat ccacccctgc atggcaccca   1680
tacccaggac ctcagggagt gccacacgat cccgctcatc ctgagaccaa gcatttcctg   1740
tattgctccg ggggacgcga acgactgcga ccatcttttc tgctgagtgc cctgcctcca   1800
tctctgaccg gggctaggaa actggtggag acaatctttc tgggaagtgc cccacagaag   1860
ccaggagcag ctcgacgaat gagaaggctg cctgctcgct actggagaat gaggccactg   1920
ttccaggaac tgctggggaa ccacgcacgg tgcccttata gagccctgct gaggacccat   1980
tgtccactga gggccatggc agccaaggag gcaagcggaa atcaggccca ccgcggagtc   2040
ggcatttgcc ctctggaacg accagtggct gcaccagagg aacagaccga cccccgccga   2100
ctggtgcagc tgctgcgcca gcattctagt ccttggcagg tgtacgcatt cctgcgagca   2160
tgcctgtgcc gactggtgcc aacaggactg tgggggtccc gacacaacca gcggagattc   2220
ctgcggaacg tgaagaagtt catctcactg ggcaagcatg ccaaactgag cctgcaggag   2280
ctgacatgga agatgaaagt gcaggattgt gcatggctga ggggaagccc aggagcatgc   2340
tgcgtgccag cagctgaaca caggcgccga gaggaaattc tggcccggtt cctggtgtgg   2400
ctgatgggac atatctacgt ggtcgagctg ctgagaagct tcttttatgt gaccgaaact   2460
acctttcaga agaactacct gttcttttat cgcaaaagcg tgtggtcaca gctgcagtcc   2520
atcggcatta gacagcactt caatagtgtc catctgaggg agctgtcaga ggccgaagtg   2580
cggagacaca gagaagccag gcctgctctg ctgacatccc gcctgcgatt cctgccagct   2640
ccctctggcc tggcaccaat tgtcaacatg gactacgtga tgggggcccg cactttccac   2700
cgagataaga aagtgcagca tctgaccagc caggtcaaaa cactgttttc cgtgctgaat   2760
tatgagcgag ctaggcgccc ctctctgctg ggagcaagtg tgctgggaat ggacgatatc   2820
caccgagcat ggcgaacctt cgtcctgcgg gtgagagctc aggaccctgc accacagctg   2880
tactttgtga aggtcgctgt gacaggagca gcagacgcac tgccacagga tagactggtc   2940
gaagtgatcg ccaacgtcat tcgcccccag gaaaatactt actgcgtgcg gcactatgct   3000
gtggtccgac gaaccgcacg aggacacgtc agaaagtcct tcaaacggca cgtgagcacc   3060
ttcaccgacc tgcagcccta tatgcgccag tttgtggagc ggctgcagga aacatcaagc   3120
ctgagagatg ccgtggtcat tgagcagtcc tctagtctga acgaagctgg gtccggactg   3180
ttccacctgt ttctgagact ggtccacaat catgtgatca ggattggcgg gaaaagttac   3240
atccagtgtc agggcattcc tcaggggagc atcctgtcca ccctgctgtg ctcactgtgc   3300
tatggcgaca tggagagaag gctgttccca ggcatccagc aggacggggt cctgctgcga   3360
ctggtggccg atttcctgct ggtgacacct cacctgactc aggcccaggc ttttctgagg   3420
acactggtcc gcggcgtgcc agagtacgga tgcagagcca acctgcagaa gactgctgtc   3480
aatttccctg tggaagatgg ggccctggga tctgctgcac ctctgcagct gccagctcat   3540
tgcctgtttc catggtgtgg cctgctgctg gacaccagga cactggaagt gagctgtgat   3600
tactcaagct atgcacgaac atcaattcgg gccagcctga ctttttccca gggagccaag   3660
cccggcagaa acatgcgccg aaaactgttc gccgtgctga ggctgaagtg ctgtgctctg   3720
```

-continued

```
tttctgtacc tgcaggtgaa cagcattcac acagtctaca tgaacgtgta caaaatcttc   3780
ctgctgcagg cctatcggtt tcatgcttgc gtcctgcagc tgcccttcaa ccagcctgtg   3840
cgcaagaatc ctagtttctt tctgagagtg atctctgata ctgccagttg ctgttactca   3900
ctgctgaaag caaggaatgc cggcatgtct ctgggcgcta agggggcatc aggactgttc   3960
ccaagcgagg cagctcgatg gctgtgcctg cacgcttttc tgctgaaact ggcaagacat   4020
tccgggactt ataggtgtct gctgggagcc ctgagagcag ccaaggctca cctgtctaga   4080
cagctgccca ggggcaccct ggccgcactg gaagcagcag cagacccaag cctgaccgca   4140
gatttcaaaa ctatcctgga ctgagcggcc gctcgagtct agagggcccg tttaaacccg   4200
ctgatcagcc tcgactgtgc cttctagttg ccagccatct gttgtttgcc cctcccccgt   4260
gccttccttg accctggaag gtgccactcc cactgtcctt tcctaataaa atgaggaaat   4320
tgcatcgcat tgtctgagta ggtgtcattc tattctgggg ggtggggtgg ggcaggacag   4380
caagggggag gattgggaag acaatagcag gcatgctggg gatgcggtgg gctctatggc   4440
ttctactggg cggttttatg gacagcaagc gaaccggaat tgccagctgg ggcgccctct   4500
ggtaaggttg ggaagccctg caaagtaaac tggatggctt tcttgccgcc aaggatctga   4560
tggcgcaggg gatcaagctc tgatcaagag acaggatgag gatcgtttcg catgattgaa   4620
caagatggat tgcacgcagg ttctccggcc gcttgggtgg agaggctatt cggctatgac   4680
tgggcacaac agacaatcgg ctgctctgat gccgccgtgt tccggctgtc agcgcagggg   4740
cgcccggttc tttttgtcaa gaccgacctg tccggtgccc tgaatgaact gcaagacgag   4800
gcagcgcggc tatcgtggct ggccacgacg ggcgttcctt gcgcagctgt gctcgacgtt   4860
gtcactgaag cgggaaggga ctggctgcta ttgggcgaag tgccggggca ggatctcctg   4920
tcatctcacc ttgctcctgc cgagaaagta tccatcatgg ctgatgcaat gcggcggctg   4980
catacgcttg atccggctac ctgcccattc gaccaccaag cgaaacatcg catcgagcga   5040
gcacgtactc ggatggaagc cggtcttgtc gatcaggatg atctggacga agagcatcag   5100
gggctcgcgc cagccgaact gttcgccagg ctcaaggcga gcatgcccga cggcgaggat   5160
ctcgtcgtga cccatggcga tgcctgcttg ccgaatatca tggtggaaaa tggccgcttt   5220
tctggattca tcgactgtgg ccggctgggt gtggcggacc gctatcagga catagcgttg   5280
gctacccgtg atattgctga agagcttggc ggcgaatggg ctgaccgctt cctcgtgctt   5340
tacggtatcg ccgctcccga ttcgcagcgc atcgccttct atcgccttct tgacgagttc   5400
ttctgaatta ttaacgctta caatttcctg atgcggtatt ttctccttac gcatctgtgc   5460
ggtatttcac accgcatcag gtggcacttt tcggggaaat gtgcgcggaa cccctatttg   5520
tttatttttc taaatacatt caaatatgta tccgctcatg agacaataac cctgataaat   5580
gcttcaataa tagcacgtgc taaaacttca tttttaattt aaaaggatct aggtgaagat   5640
cctttttgat aatctcatga ccaaaatccc ttaacgtgag ttttcgttcc actgagcgtc   5700
agaccccgta gaaaagatca aaggatcttc ttgagatcct ttttttctgc gcgtaatctg   5760
ctgcttgcaa acaaaaaaac caccgctacc agcggtggtt tgtttgccgg atcaagagct   5820
accaactctt tttccgaagg taactggctt cagcagagcg cagataccaa atactgttct   5880
tctagtgtag ccgtagttag gccaccactt caagaactct gtagcaccgc ctacatacct   5940
cgctctgcta atcctgttac cagtggctgc tgccagtggc gataagtcgt gtcttaccgg   6000
gttggactca agacgatagt taccggataa ggcgcagcgg tcgggctgaa cggggggttc   6060
gtgcacacag cccagcttgg agcgaacgac ctacaccgaa ctgagatacc tacagcgtga   6120
```

```
gctatgagaa agcgccacgc ttcccgaagg gagaaaggcg gacaggtatc cggtaagcgg   6180

cagggtcgga acaggagagc gcacgaggga gcttccaggg ggaaacgcct ggtatcttta   6240

tagtcctgtc gggtttcgcc acctctgact tgagcgtcga tttttgtgat gctcgtcagg   6300

ggggcggagc ctatggaaaa acgccagcaa cgcggccttt ttacggttcc tggccttttg   6360

ctggcctttt gctcacatgt tctt                                          6384
```

<210> SEQ ID NO 4
<211> LENGTH: 3444
<212> TYPE: DNA
<213> ORGANISM: Artificial Sequence
<220> FEATURE:
<223> OTHER INFORMATION: dTERT pGX1415 insert

<400> SEQUENCE: 4

```
ggatccgcca ccatggactg gacttggatt ctgttcctgg tcgctgccgc cactcgcgtg     60

cattcacctc gggctcctcg ctgtagggct gtgcgggctc tgctgagagg ccggtacagg    120

gaggtgctgc cactggccac cttcctgagg agactgggcc ctcccggcag actgctggtg    180

cggcgcggcg accctgcagc ctttcgggcc ctggtggcac agtgcctggt gtgcgtgcca    240

tggggcgccc gcccaccccc tgcagcacca tgctttaggc aggtgagctg tctgaaggag    300

ctggtggccc gcgtggtgca gaggctgtgc gagagaggcg ccaggaacgt gctggccttc    360

ggctttgccc tgctggatgg agcccgcggc ggcccacccg tggccttcac cacaagcgtg    420

aggtcctacc tgcctaatac cgtgacagag acactgagag gctccggagc atggggcctg    480

ctgctgagga gagtgggcga cgatgtgctg acacacctgc tggcaaggtg cgcactgtat    540

ctgctggtgg caccatcctg cgcataccag gtgtgcggcc ctccactgta tgacctgtgc    600

gcccctgcct ctctgcccct gcctgcccca ggcctgcctg gcctgccagg cctgccaggc    660

ctgggagcag gagcaggagc cagcgccgat ctgcgcccaa ccaggcaggc acagaactcc    720

ggagcacggc gcaggagagg ctctccaggc agcggcgtgc cctggccaa gaggcctcgg     780

cgctccgtgg catctgagcc agagagaggc gcccaccggt ccttccctcg cgcccagcag    840

cctcccgtga gcgaggcccc agccgtgaca ccagcagtgg cagcatcccc agcagcctct    900

tgggagggcg gcccacccgg cacccggcct accacaccag catggcaccc ataccctgga    960

ccacagggag tgccacacga ccctgcccac ccagagacaa agaggttcct gtattgtagc   1020

ggcggcaggg agagactgcg gcctagcttt ctgctgtccg ccctgcctcc aacactgtct   1080

ggcgccagga agctggtgga gacaatcttt ctgggcagcg cccctcagaa gcctggagca   1140

gcaaggagaa tgcggcgcct gcctgccaga tactggcgca tgaggccact gttccaggag   1200

ctgctgggaa accacgcaag gtgcccttat agagccctgc tgcggacaca ctgtccactg   1260

agagccatgg ccgccaagga gggctctggc aatcaggccc acagaggcgt gggaatctgc   1320

cctctggagc ggccagtggc agcccctcag gagcagacag atagcaccag gctggtgcag   1380

ctgctgaggc agcacagctc ccatggcag gtgtacgcct tcctgagggc atgcctgtgc    1440

tggctggtgc caaccggcct gtggggctcc agacacaacc agaggagatt cctgcggaat   1500

gtgaagaagt ttatcagcct gggcaagcac gccaagctgt ccctgcagga gctgacatgg   1560

aagatgaagg tgagagactg tacctggctg cacggcaacc caggcgcctg ctgcgtgcca   1620

gcagcagagc accggcgcag ggaggagatc ctggcaaggt tcctggtgct ggtggatggc   1680

cacatctacg tggtgaagct gctgagatcc ttcttttatg tgaccgagac tacgttccag   1740
```

```
aagaactacc tgttctttta tcggaagagc gtgtggtccc agctgcagtc tatcggcatc   1800
cgccagctgt tcaattctgt gcacctgagg gagctgagcg aggcagaggt gagacggcac   1860
agagaggccc ggccagccct gctgacatct agactgcggt tcctgccagc acctagcggc   1920
ctggccccca tcgtgaacat ggactacatc atgggcgccc gcaccttcca cagggataag   1980
aaggtgcagc acctgacatc ccagctgaag accctgtttt ctgtgctgaa ttatgagagg   2040
gcacgcaggc cttccctgct gggagcctct atgctgggca tggacgatat ccaccgcgcc   2100
tggaggacat tcgtgctgcg catcagggca cagaacccag cccctcagct gtactttgtg   2160
aaggtggcag tgaccggagc agcagacgca ctgccccagg atcgcctggt ggaagtgatc   2220
gccaatgtga tcagacctca ggagagcaca tactgcgtgc ggcactatgc agtggtgcag   2280
agaaccgcca ggggccacgt gcgcaaggcc ttcaagaggc acgtgtccac atttgccgac   2340
ctgcagccat atatgagaca gtttgtggag cggctgcagg agacaagcct gctgagggat   2400
gccgtggtca tcgagcagtc tagctccctg aacgaggccg gctctagcct gttccacctg   2460
tttctgcgcc tggtgcacaa tcacgtggtg aggatcggcg gcaagtctta catccagtgt   2520
cagggcgtgc cccagggctc tatcctgagc accctgctgt gcagcctgtg ctatggcgac   2580
atggagagac ggctgttccc tggcatcgag caggacggcg tgctgctgag actggtggcc   2640
gatttcctgc tggtgacacc acacctgacc caggcccagg cctttctgcg gacactggtg   2700
aagggagtgc ctgagtacgg atgcagggca aacctgcaga agaccgccgt gaatttccca   2760
gtggaggatg gcgccctggg cagcgccgcc cctctgcagc tgccagccca ctgcctgttt   2820
ccatggtgtg gcctgctgct ggacacacgg accctggagg tgtcctgtga ttactcctct   2880
tatgcccaca catctatcag ggcaagcctg accttttccc agggagcaaa gccaggaagg   2940
aacatgcgca ggaagctgct ggccgtgctg aggctgaagt gctgtgccct gttcctgtac   3000
ctgcaggtga acggcatcca cacagtgtac atgaacgtgt acaagatctt cctgctgcag   3060
gcctatcggt ttcacgcctg cgtgctgcag ctgcccttca accagcctgt gagaaagaat   3120
cctagcttct ttctgagagt gatcgccgac accgcctctt gctgttacag cctgctgaag   3180
gcccgcaatg caggcctgtc cctgggagca aagggagcaa gcggcctgtt cccatccgag   3240
gcagcaaggt ggctgtgcct gcacgccttt ctgctgaagc tggcccacca cagcggcaca   3300
tatagatgtc tgctgggcgc cctgcaggca gcaaaggcac acctgtccag acagctgccc   3360
cggggcaccc tggcagccct ggaggcagcc gcagaccctt cactgacagc cgacttcaag   3420
acaatcctgg actgataact cgag                                          3444
```

<210> SEQ ID NO 5
<211> LENGTH: 1140
<212> TYPE: PRT
<213> ORGANISM: Artificial Sequence
<220> FEATURE:
<223> OTHER INFORMATION: dTERT pGX1415 insert

<400> SEQUENCE: 5

```
Met Asp Trp Thr Trp Ile Leu Phe Leu Val Ala Ala Ala Thr Arg Val
1               5                   10                  15

His Ser Pro Arg Ala Pro Arg Cys Arg Ala Val Arg Ala Leu Leu Arg
            20                  25                  30

Gly Arg Tyr Arg Glu Val Leu Pro Leu Ala Thr Phe Leu Arg Arg Leu
        35                  40                  45

Gly Pro Pro Gly Arg Leu Leu Val Arg Arg Gly Asp Pro Ala Ala Phe
    50                  55                  60
```

```
Arg Ala Leu Val Ala Gln Cys Leu Val Cys Val Pro Trp Gly Ala Arg
65                  70                  75                  80

Pro Pro Pro Ala Ala Pro Cys Phe Arg Gln Val Ser Cys Leu Lys Glu
                85                  90                  95

Leu Val Ala Arg Val Val Gln Arg Leu Cys Glu Arg Gly Ala Arg Asn
            100                 105                 110

Val Leu Ala Phe Gly Phe Ala Leu Leu Asp Gly Ala Arg Gly Gly Pro
        115                 120                 125

Pro Val Ala Phe Thr Thr Ser Val Arg Ser Tyr Leu Pro Asn Thr Val
    130                 135                 140

Thr Glu Thr Leu Arg Gly Ser Gly Ala Trp Gly Leu Leu Leu Arg Arg
145                 150                 155                 160

Val Gly Asp Asp Val Leu Thr His Leu Leu Ala Arg Cys Ala Leu Tyr
                165                 170                 175

Leu Leu Val Ala Pro Ser Cys Ala Tyr Gln Val Cys Gly Pro Pro Leu
            180                 185                 190

Tyr Asp Leu Cys Ala Pro Ala Ser Leu Pro Leu Pro Ala Pro Gly Leu
        195                 200                 205

Pro Gly Leu Pro Gly Leu Pro Gly Leu Gly Ala Gly Ala Gly Ala Ser
    210                 215                 220

Ala Asp Leu Arg Pro Thr Arg Gln Ala Gln Asn Ser Gly Ala Arg Arg
225                 230                 235                 240

Arg Arg Gly Ser Pro Gly Ser Gly Val Pro Leu Ala Lys Arg Pro Arg
                245                 250                 255

Arg Ser Val Ala Ser Glu Pro Glu Arg Gly Ala His Arg Ser Phe Pro
            260                 265                 270

Arg Ala Gln Gln Pro Pro Val Ser Glu Ala Pro Ala Val Thr Pro Ala
        275                 280                 285

Val Ala Ala Ser Pro Ala Ala Ser Trp Glu Gly Gly Pro Pro Gly Thr
    290                 295                 300

Arg Pro Thr Thr Pro Ala Trp His Pro Tyr Pro Gly Pro Gln Gly Val
305                 310                 315                 320

Pro His Asp Pro Ala His Pro Glu Thr Lys Arg Phe Leu Tyr Cys Ser
                325                 330                 335

Gly Gly Arg Glu Arg Leu Arg Pro Ser Phe Leu Leu Ser Ala Leu Pro
            340                 345                 350

Pro Thr Leu Ser Gly Ala Arg Lys Leu Val Glu Thr Ile Phe Leu Gly
        355                 360                 365

Ser Ala Pro Gln Lys Pro Gly Ala Ala Arg Arg Met Arg Arg Leu Pro
    370                 375                 380

Ala Arg Tyr Trp Arg Met Arg Pro Leu Phe Gln Glu Leu Leu Gly Asn
385                 390                 395                 400

His Ala Arg Cys Pro Tyr Arg Ala Leu Leu Arg Thr His Cys Pro Leu
                405                 410                 415

Arg Ala Met Ala Ala Lys Glu Gly Ser Gly Asn Gln Ala His Arg Gly
            420                 425                 430

Val Gly Ile Cys Pro Leu Glu Arg Pro Val Ala Ala Pro Gln Glu Gln
        435                 440                 445

Thr Asp Ser Thr Arg Leu Val Gln Leu Leu Arg Gln His Ser Ser Pro
    450                 455                 460

Trp Gln Val Tyr Ala Phe Leu Arg Ala Cys Leu Cys Trp Leu Val Pro
465                 470                 475                 480
```

```
Thr Gly Leu Trp Gly Ser Arg His Asn Gln Arg Arg Phe Leu Arg Asn
                485                 490                 495

Val Lys Lys Phe Ile Ser Leu Gly Lys His Ala Lys Leu Ser Leu Gln
            500                 505                 510

Glu Leu Thr Trp Lys Met Lys Val Arg Asp Cys Thr Trp Leu His Gly
        515                 520                 525

Asn Pro Gly Ala Cys Cys Val Pro Ala Ala Glu His Arg Arg Arg Glu
    530                 535                 540

Glu Ile Leu Ala Arg Phe Leu Val Leu Val Asp Gly His Ile Tyr Val
545                 550                 555                 560

Val Lys Leu Leu Arg Ser Phe Phe Tyr Val Thr Glu Thr Thr Phe Gln
                565                 570                 575

Lys Asn Tyr Leu Phe Phe Tyr Arg Lys Ser Val Trp Ser Gln Leu Gln
            580                 585                 590

Ser Ile Gly Ile Arg Gln Leu Phe Asn Ser Val His Leu Arg Glu Leu
        595                 600                 605

Ser Glu Ala Glu Val Arg Arg His Arg Glu Ala Arg Pro Ala Leu Leu
    610                 615                 620

Thr Ser Arg Leu Arg Phe Leu Pro Ala Pro Ser Gly Leu Ala Pro Ile
625                 630                 635                 640

Val Asn Met Asp Tyr Ile Met Gly Ala Arg Thr Phe His Arg Asp Lys
                645                 650                 655

Lys Val Gln His Leu Thr Ser Gln Leu Lys Thr Leu Phe Ser Val Leu
            660                 665                 670

Asn Tyr Glu Arg Ala Arg Arg Pro Ser Leu Leu Gly Ala Ser Met Leu
        675                 680                 685

Gly Met Asp Asp Ile His Arg Ala Trp Arg Thr Phe Val Leu Arg Ile
    690                 695                 700

Arg Ala Gln Asn Pro Ala Pro Gln Leu Tyr Phe Val Lys Val Ala Val
705                 710                 715                 720

Thr Gly Ala Ala Asp Ala Leu Pro Gln Asp Arg Leu Val Glu Val Ile
                725                 730                 735

Ala Asn Val Ile Arg Pro Gln Glu Ser Thr Tyr Cys Val Arg His Tyr
            740                 745                 750

Ala Val Val Gln Arg Thr Ala Arg Gly His Val Arg Lys Ala Phe Lys
        755                 760                 765

Arg His Val Ser Thr Phe Ala Asp Leu Gln Pro Tyr Met Arg Gln Phe
    770                 775                 780

Val Glu Arg Leu Gln Glu Thr Ser Leu Leu Arg Asp Ala Val Val Ile
785                 790                 795                 800

Glu Gln Ser Ser Ser Leu Asn Glu Ala Gly Ser Ser Leu Phe His Leu
                805                 810                 815

Phe Leu Arg Leu Val His Asn His Val Val Arg Ile Gly Gly Lys Ser
            820                 825                 830

Tyr Ile Gln Cys Gln Gly Val Pro Gln Gly Ser Ile Leu Ser Thr Leu
        835                 840                 845

Leu Cys Ser Leu Cys Tyr Gly Asp Met Glu Arg Arg Leu Phe Pro Gly
    850                 855                 860

Ile Glu Gln Asp Gly Val Leu Leu Arg Leu Val Ala Asp Phe Leu Leu
865                 870                 875                 880

Val Thr Pro His Leu Thr Gln Ala Gln Ala Phe Leu Arg Thr Leu Val
                885                 890                 895

Lys Gly Val Pro Glu Tyr Gly Cys Arg Ala Asn Leu Gln Lys Thr Ala
```

```
        900                 905                 910

Val Asn Phe Pro Val Glu Asp Gly Ala Leu Gly Ser Ala Ala Pro Leu
        915                 920                 925

Gln Leu Pro Ala His Cys Leu Phe Pro Trp Cys Gly Leu Leu Leu Asp
    930                 935                 940

Thr Arg Thr Leu Glu Val Ser Cys Asp Tyr Ser Ser Tyr Ala His Thr
945                 950                 955                 960

Ser Ile Arg Ala Ser Leu Thr Phe Ser Gln Gly Ala Lys Pro Gly Arg
                965                 970                 975

Asn Met Arg Arg Lys Leu Leu Ala Val Leu Arg Leu Lys Cys Cys Ala
            980                 985                 990

Leu Phe Leu Tyr Leu Gln Val Asn  Gly Ile His Thr Val  Tyr Met Asn
        995                 1000                1005

Val Tyr  Lys Ile Phe Leu Leu  Gln Ala Tyr Arg Phe  His Ala Cys
    1010                 1015                 1020

Val Leu  Gln Leu Pro Phe Asn  Gln Pro Val Arg Lys  Asn Pro Ser
    1025                 1030                 1035

Phe Phe  Leu Arg Val Ile Ala  Asp Thr Ala Ser Cys  Cys Tyr Ser
    1040                 1045                 1050

Leu Leu  Lys Ala Arg Asn Ala  Gly Leu Ser Leu Gly  Ala Lys Gly
    1055                 1060                 1065

Ala Ser  Gly Leu Phe Pro Ser  Glu Ala Ala Arg Trp  Leu Cys Leu
    1070                 1075                 1080

His Ala  Phe Leu Leu Lys Leu  Ala His His Ser Gly  Thr Tyr Arg
    1085                 1090                 1095

Cys Leu  Leu Gly Ala Leu Gln  Ala Ala Lys Ala His  Leu Ser Arg
    1100                 1105                 1110

Gln Leu  Pro Arg Gly Thr Leu  Ala Ala Leu Glu Ala  Ala Ala Asp
    1115                 1120                 1125

Pro Ser  Leu Thr Ala Asp Phe  Lys Thr Ile Leu Asp
    1130                 1135                 1140


<210> SEQ ID NO 6
<211> LENGTH: 15
<212> TYPE: PRT
<213> ORGANISM: Canis familiaris
<220> FEATURE:
<221> NAME/KEY: MISC_FEATURE
<222> LOCATION: (1)..(15)
<223> OTHER INFORMATION: Native dTERT epitope

<400> SEQUENCE: 6

Phe Asn Ser Val His Leu Arg Glu Leu Ser Glu Ala Glu Val Arg
1               5                   10                  15


<210> SEQ ID NO 7
<211> LENGTH: 1140
<212> TYPE: PRT
<213> ORGANISM: Canis familiaris
<220> FEATURE:
<221> NAME/KEY: MISC_FEATURE
<222> LOCATION: (1)..(1140)
<223> OTHER INFORMATION: Native dTERT

<400> SEQUENCE: 7

Met Asp Trp Thr Trp Ile Leu Phe Leu Val Ala Ala Ala Thr Arg Val
1               5                   10                  15

His Ser Pro Arg Ala Pro Arg Cys Arg Ala Val Arg Ala Leu Leu Arg
            20                  25                  30
```

```
Gly Arg Tyr Arg Glu Val Leu Pro Leu Ala Thr Phe Leu Arg Arg Leu
        35                  40                  45

Gly Pro Pro Gly Arg Leu Leu Val Arg Arg Gly Asp Pro Ala Ala Phe
    50                  55                  60

Arg Ala Leu Val Ala Gln Cys Leu Val Cys Val Pro Trp Gly Ala Arg
65                  70                  75                  80

Pro Pro Pro Ala Ala Pro Cys Phe Arg Gln Val Ser Cys Leu Lys Glu
                85                  90                  95

Leu Val Ala Arg Val Val Gln Arg Leu Cys Glu Arg Gly Ala Arg Asn
            100                 105                 110

Val Leu Ala Phe Gly Phe Ala Leu Leu Asp Gly Ala Arg Gly Gly Pro
        115                 120                 125

Pro Val Ala Phe Thr Thr Ser Val Arg Ser Tyr Leu Pro Asn Thr Val
    130                 135                 140

Thr Glu Thr Leu Arg Gly Ser Gly Ala Trp Gly Leu Leu Leu Arg Arg
145                 150                 155                 160

Val Gly Asp Asp Val Leu Thr His Leu Leu Ala Arg Cys Ala Leu Tyr
                165                 170                 175

Leu Leu Val Ala Pro Ser Cys Ala Tyr Gln Val Cys Gly Pro Pro Leu
            180                 185                 190

Tyr Asp Leu Cys Ala Pro Ala Ser Leu Pro Leu Pro Ala Pro Gly Leu
        195                 200                 205

Pro Gly Leu Pro Gly Leu Pro Gly Leu Gly Ala Gly Ala Gly Ala Ser
    210                 215                 220

Ala Asp Leu Arg Pro Thr Arg Gln Ala Gln Asn Ser Gly Ala Arg Arg
225                 230                 235                 240

Arg Arg Gly Ser Pro Gly Ser Gly Val Pro Leu Ala Lys Arg Pro Arg
                245                 250                 255

Arg Ser Val Ala Ser Glu Pro Glu Arg Gly Ala His Arg Ser Phe Pro
            260                 265                 270

Arg Ala Gln Gln Pro Pro Val Ser Glu Ala Pro Ala Val Thr Pro Ala
        275                 280                 285

Val Ala Ala Ser Pro Ala Ala Ser Trp Glu Gly Gly Pro Pro Gly Thr
    290                 295                 300

Arg Pro Thr Thr Pro Ala Trp His Pro Tyr Pro Gly Pro Gln Gly Val
305                 310                 315                 320

Pro His Asp Pro Ala His Pro Glu Thr Lys Arg Phe Leu Tyr Cys Ser
                325                 330                 335

Gly Gly Arg Glu Arg Leu Arg Pro Ser Phe Leu Leu Ser Ala Leu Pro
            340                 345                 350

Pro Thr Leu Ser Gly Ala Arg Lys Leu Val Glu Thr Ile Phe Leu Gly
        355                 360                 365

Ser Ala Pro Gln Lys Pro Gly Ala Ala Arg Arg Met Arg Arg Leu Pro
    370                 375                 380

Ala Arg Tyr Trp Arg Met Arg Pro Leu Phe Gln Glu Leu Leu Gly Asn
385                 390                 395                 400

His Ala Arg Cys Pro Tyr Arg Ala Leu Leu Arg Thr His Cys Pro Leu
                405                 410                 415

Arg Ala Met Ala Ala Lys Glu Gly Ser Gly Asn Gln Ala His Arg Gly
            420                 425                 430

Val Gly Ile Cys Pro Leu Glu Arg Pro Val Ala Ala Pro Gln Glu Gln
        435                 440                 445
```

```
Thr Asp Ser Thr Arg Leu Val Gln Leu Leu Arg Gln His Ser Ser Pro
    450                 455                 460

Trp Gln Val Tyr Ala Phe Leu Arg Ala Cys Leu Cys Trp Leu Val Pro
465                 470                 475                 480

Thr Gly Leu Trp Gly Ser Arg His Asn Gln Arg Arg Phe Leu Arg Asn
                485                 490                 495

Val Lys Lys Phe Ile Ser Leu Gly Lys His Ala Lys Leu Ser Leu Gln
            500                 505                 510

Glu Leu Thr Trp Lys Met Lys Val Arg Asp Cys Thr Trp Leu His Gly
        515                 520                 525

Asn Pro Gly Ala Cys Cys Val Pro Ala Ala Glu His Arg Arg Arg Glu
    530                 535                 540

Glu Ile Leu Ala Arg Phe Leu Val Leu Val Asp Gly His Ile Tyr Val
545                 550                 555                 560

Val Lys Leu Leu Arg Ser Phe Phe Tyr Val Thr Glu Thr Thr Phe Gln
                565                 570                 575

Lys Asn Tyr Leu Phe Phe Tyr Arg Lys Ser Val Trp Ser Gln Leu Gln
            580                 585                 590

Ser Ile Gly Ile Arg Gln Leu Phe Asn Ser Val His Leu Arg Glu Leu
        595                 600                 605

Ser Glu Ala Glu Val Arg Arg His Arg Glu Ala Arg Pro Ala Leu Leu
    610                 615                 620

Thr Ser Arg Leu Arg Phe Leu Pro Ala Pro Ser Gly Leu Ala Pro Ile
625                 630                 635                 640

Val Asn Met Asp Tyr Ile Met Gly Ala Arg Thr Phe His Arg Asp Lys
                645                 650                 655

Lys Val Gln His Leu Thr Ser Gln Leu Lys Thr Leu Phe Ser Val Leu
            660                 665                 670

Asn Tyr Glu Arg Ala Arg Arg Pro Ser Leu Leu Gly Ala Ser Met Leu
        675                 680                 685

Gly Met Asp Asp Ile His Arg Ala Trp Arg Thr Phe Val Leu Arg Ile
    690                 695                 700

Arg Ala Gln Asn Pro Ala Pro Gln Leu Tyr Phe Val Lys Val Ala Val
705                 710                 715                 720

Thr Gly Ala Ala Asp Ala Leu Pro Gln Asp Arg Leu Val Glu Val Ile
                725                 730                 735

Ala Asn Val Ile Arg Pro Gln Glu Ser Thr Tyr Cys Val Arg His Tyr
            740                 745                 750

Ala Val Val Gln Arg Thr Ala Arg Gly His Val Arg Lys Ala Phe Lys
        755                 760                 765

Arg His Val Ser Thr Phe Ala Asp Leu Gln Pro Tyr Met Arg Gln Phe
    770                 775                 780

Val Glu Arg Leu Gln Glu Thr Ser Leu Leu Arg Asp Ala Val Val Ile
785                 790                 795                 800

Glu Gln Ser Ser Ser Leu Asn Glu Ala Gly Ser Ser Leu Phe His Leu
                805                 810                 815

Phe Leu Arg Leu Val His Asn His Val Val Arg Ile Gly Gly Lys Ser
            820                 825                 830
```

-continued

```
Tyr Ile Gln Cys Gln Gly Val Pro Gln Gly Ser Ile Leu Ser Thr Leu
        835                 840                 845

Leu Cys Ser Leu Cys Tyr Gly Asp Met Glu Arg Arg Leu Phe Pro Gly
    850                 855                 860

Ile Glu Gln Asp Gly Val Leu Leu Arg Leu Val Ala Asp Phe Leu Leu
865                 870                 875                 880

Val Thr Pro His Leu Thr Gln Ala Gln Ala Phe Leu Arg Thr Leu Val
                885                 890                 895

Lys Gly Val Pro Glu Tyr Gly Cys Arg Ala Asn Leu Gln Lys Thr Ala
            900                 905                 910

Val Asn Phe Pro Val Glu Asp Gly Ala Leu Gly Ser Ala Ala Pro Leu
        915                 920                 925

Gln Leu Pro Ala His Cys Leu Phe Pro Trp Cys Gly Leu Leu Leu Asp
    930                 935                 940

Thr Arg Thr Leu Glu Val Ser Cys Asp Tyr Ser Ser Tyr Ala His Thr
945                 950                 955                 960

Ser Ile Arg Ala Ser Leu Thr Phe Ser Gln Gly Ala Lys Pro Gly Arg
                965                 970                 975

Asn Met Arg Arg Lys Leu Leu Ala Val Leu Arg Leu Lys Cys Cys Ala
            980                 985                 990

Leu Phe Leu Tyr Leu Gln Val Asn  Gly Ile His Thr Val  Tyr Met Asn
        995                 1000                1005

Val Tyr  Lys Ile Phe Leu Leu  Gln Ala Tyr Arg Phe  His Ala Cys
    1010                1015                1020

Val Leu  Gln Leu Pro Phe Asn  Gln Pro Val Arg Lys  Asn Pro Ser
    1025                1030                1035

Phe Phe  Leu Arg Val Ile Ala  Asp Thr Ala Ser Cys  Cys Tyr Ser
    1040                1045                1050

Leu Leu  Lys Ala Arg Asn Ala  Gly Leu Ser Leu Gly  Ala Lys Gly
    1055                1060                1065

Ala Ser  Gly Leu Phe Pro Ser  Glu Ala Ala Arg Trp  Leu Cys Leu
    1070                1075                1080

His Ala  Phe Leu Leu Lys Leu  Ala His His Ser Gly  Thr Tyr Arg
    1085                1090                1095

Cys Leu  Leu Gly Ala Leu Gln  Ala Ala Lys Ala His  Leu Ser Arg
    1100                1105                1110

Gln Leu  Pro Arg Gly Thr Leu  Ala Ala Leu Glu Ala  Ala Ala Asp
    1115                1120                1125

Pro Ser  Leu Thr Ala Asp Phe  Lys Thr Ile Leu Asp
    1130                1135                1140
```